(12) United States Patent
Masuda et al.

(10) Patent No.: US 10,675,464 B2
(45) Date of Patent: Jun. 9, 2020

(54) ELECTRICAL STIMULATION THERAPY INSTRUMENT

(71) Applicant: OTSUKA TECHNO CORPORATION, Naruto-shi, Tokushima (JP)

(72) Inventors: Tetsuya Masuda, Naruto (JP); Nobuo Tsukui, Naruto (JP)

(73) Assignee: OTSUKA TECHNO CORPORATION, Tokushima (JP)

( * ) Notice: Subject to any disclaimer, the term of this patent is extended or adjusted under 35 U.S.C. 154(b) by 0 days.

(21) Appl. No.: 16/333,537

(22) PCT Filed: Jul. 2, 2018

(86) PCT No.: PCT/JP2018/025114
§ 371 (c)(1),
(2) Date: Mar. 14, 2019

(87) PCT Pub. No.: WO2019/021754
PCT Pub. Date: Jan. 31, 2019

(65) Prior Publication Data
US 2019/0255324 A1   Aug. 22, 2019

(30) Foreign Application Priority Data

Sep. 21, 2017 (JP) ................................ 2017-181345
May 7, 2018 (JP) ................................ 2018-089397

(51) Int. Cl.
*A61N 1/36* (2006.01)
*A61N 1/04* (2006.01)
(Continued)

(52) U.S. Cl.
CPC ....... *A61N 1/36007* (2013.01); *A61N 1/0456* (2013.01); *A61N 1/0476* (2013.01);
(Continued)

(58) Field of Classification Search
USPC ............................................................. 607/4
See application file for complete search history.

(56) References Cited

U.S. PATENT DOCUMENTS 10,463,852 B2 * 11/2019 Bradley ............... A61N 1/3787
2008/0161883 A1   7/2008 Conor
(Continued)

FOREIGN PATENT DOCUMENTS

CN    2058102 U   6/1990
JP    3046118 U   2/1998
(Continued)

OTHER PUBLICATIONS

Decision to Grant a Patent issued in corresponding Japanese patent application No. 2018-535430, dated Jan. 24, 2019.
(Continued)

*Primary Examiner* — Nicole F Lavert
(74) *Attorney, Agent, or Firm* — Birch, Stewart, Kolasch & Birch LLP

(57) ABSTRACT

Provided is an electric stimulation treatment device which is capable of outputting a stimulation voltage more efficiently than a conventional device.
A urination disorder treatment device includes a pair of body-surface electrode pads 37, an indifferent electrode pad 39 which is larger in area than a body-surface electrode pad 37 with a relatively larger area, of the pair of body-surface electrode pads 37, and disposed in the vicinity of the pair of body-surface electrode pads 37, and a control portion 48 which supplies an electric signal to the pair of body-surface electrode pads 37 and the indifferent electrode pad 39. The control portion 48 executes any one of the following processing, that is, (1) a stimulation signal is output from one of the pair of body-surface electrode pads 37 with respect to a reference potential set to an average potential of the other of the pair of body-surface electrode pads 37 and the
(Continued)

indifferent electrode pad 39, (2) a stimulation signal is output from both of the pair of body-surface electrode pads 37 with respect to a reference potential set to the indifferent electrode pad 39, or (3) a stimulation signal is output from one of the pair of body-surface electrode pads 37 with respect to a reference potential set to the indifferent electrode pad 39.

12 Claims, 20 Drawing Sheets

(51) Int. Cl.
    *A61B 5/0488*     (2006.01)
    *A61B 5/20*     (2006.01)

(52) U.S. Cl.
    CPC ..... *A61N 1/36021* (2013.01); *A61N 1/36034* (2017.08); *A61B 5/04882* (2013.01); *A61B 5/202* (2013.01)

(56) References Cited

U.S. PATENT DOCUMENTS

| | | | |
|---|---|---|---|
| 2012/0197339 A1 | 8/2012 | Takagi et al. | |
| 2012/0259239 A1* | 10/2012 | Chenaux | A61B 5/04001 |
| | | | 600/554 |
| 2015/0032016 A1* | 1/2015 | Ghosh | A61B 5/6823 |
| | | | 600/516 |
| 2016/0250472 A1 | 9/2016 | Carbunaru | |
| 2017/0049513 A1* | 2/2017 | Cosman, Jr. | A61B 18/18 |
| 2017/0056652 A1 | 3/2017 | Gittard et al. | |
| 2017/0333701 A1* | 11/2017 | Bradley | A61N 1/0553 |

FOREIGN PATENT DOCUMENTS

| | | |
|---|---|---|
| JP | 2008-534041 A | 3/2007 |
| JP | 2008-534041 A | 8/2008 |
| JP | 4839457 B2 | 12/2011 |
| JP | 5548688 B2 | 7/2014 |
| JP | 5786797 B2 | 9/2015 |
| JP | 6488499 B1 | 3/2019 |
| WO | WO 2011/033750 A1 | 3/2011 |
| WO | WO 2017/023132 A1 | 2/2017 |
| WO | WO 2017/040752 A1 | 3/2017 |

OTHER PUBLICATIONS

International Search Report for PCT/JP2018/025114 (PCT/ISA/210) dated Oct. 2, 2018.
Written Opinion of the International Searching Authority for PCT/JP2018/025114 (PCT/ISA/237) dated Oct. 2, 2018.

* cited by examiner

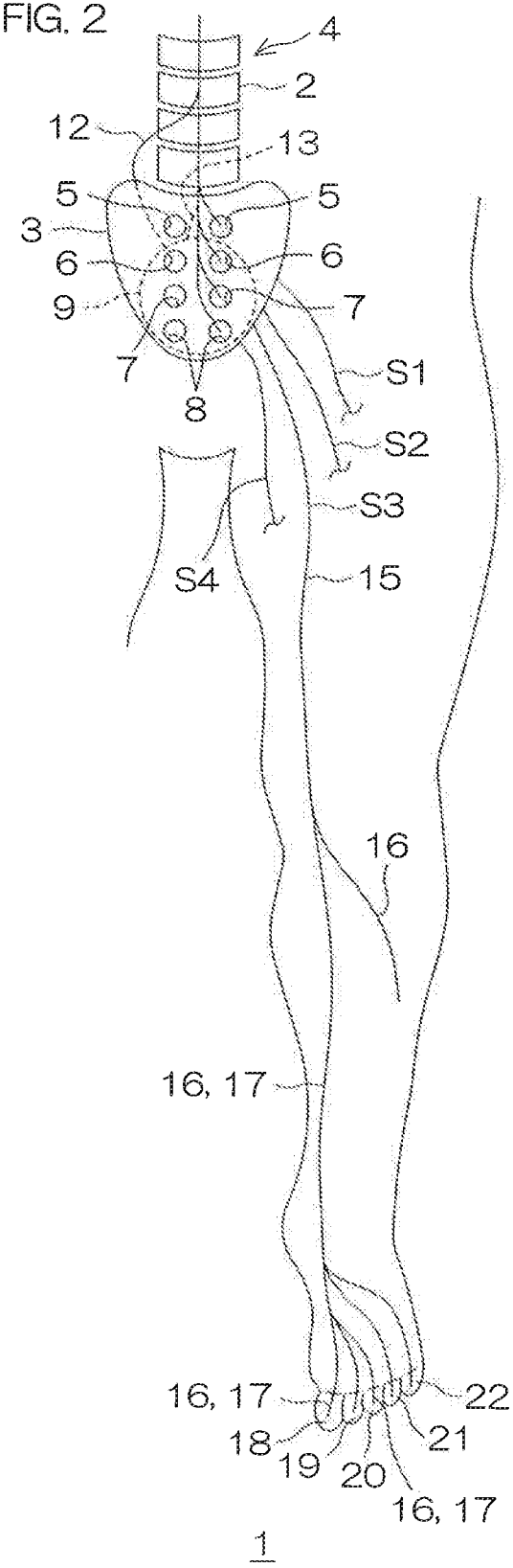

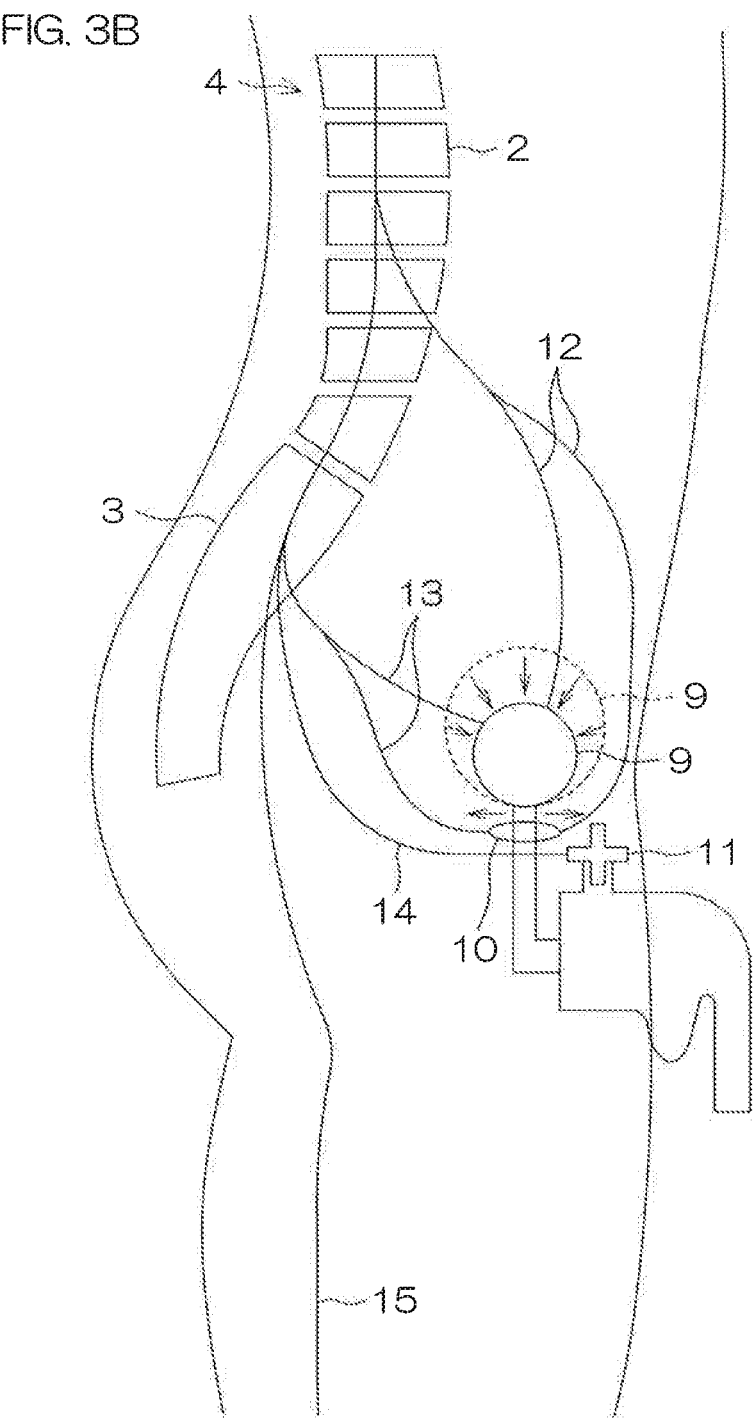

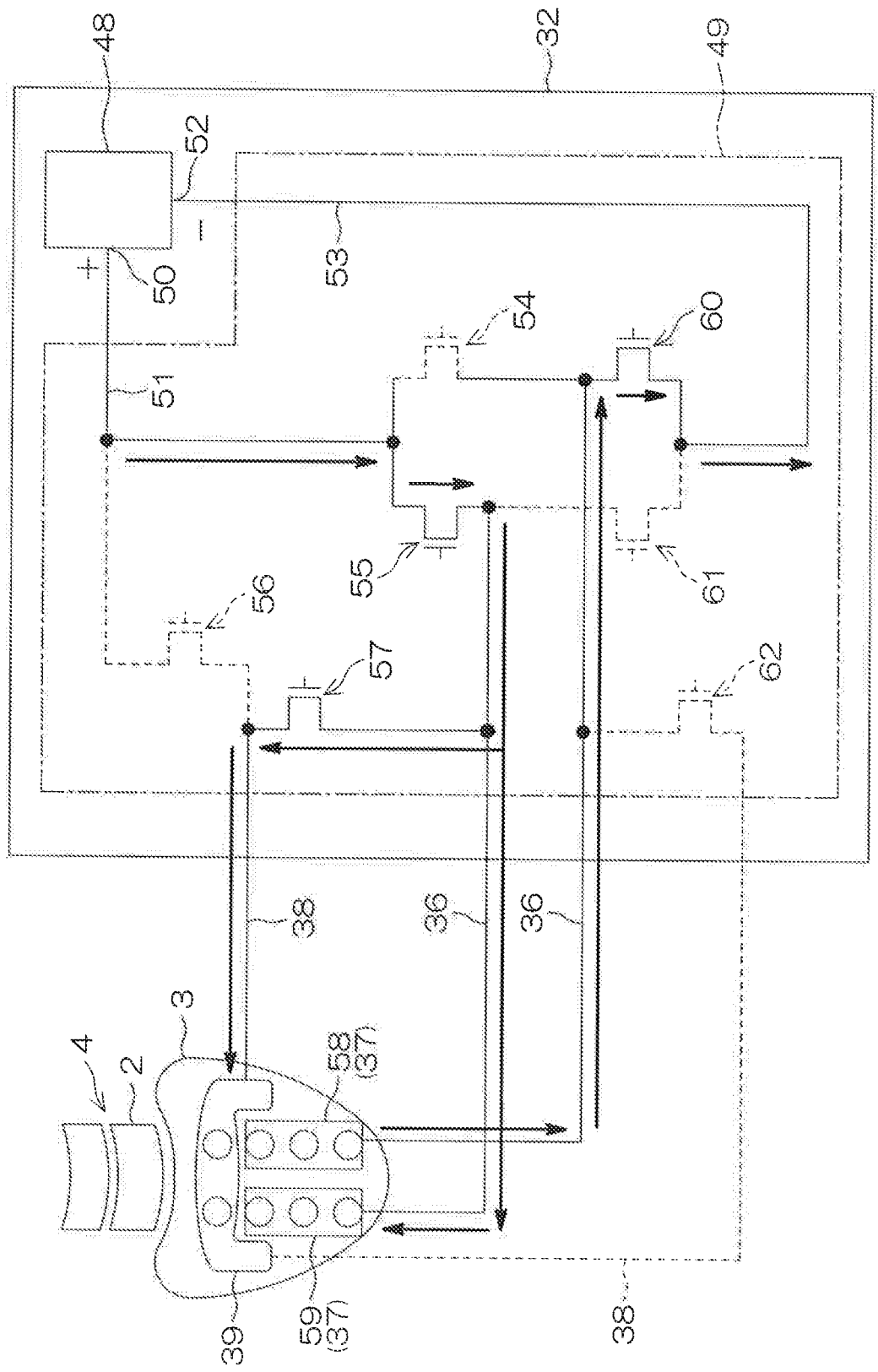
FIG. 6  ON signal when minus (−) potential is predominantly given to first stimulation electrode 58

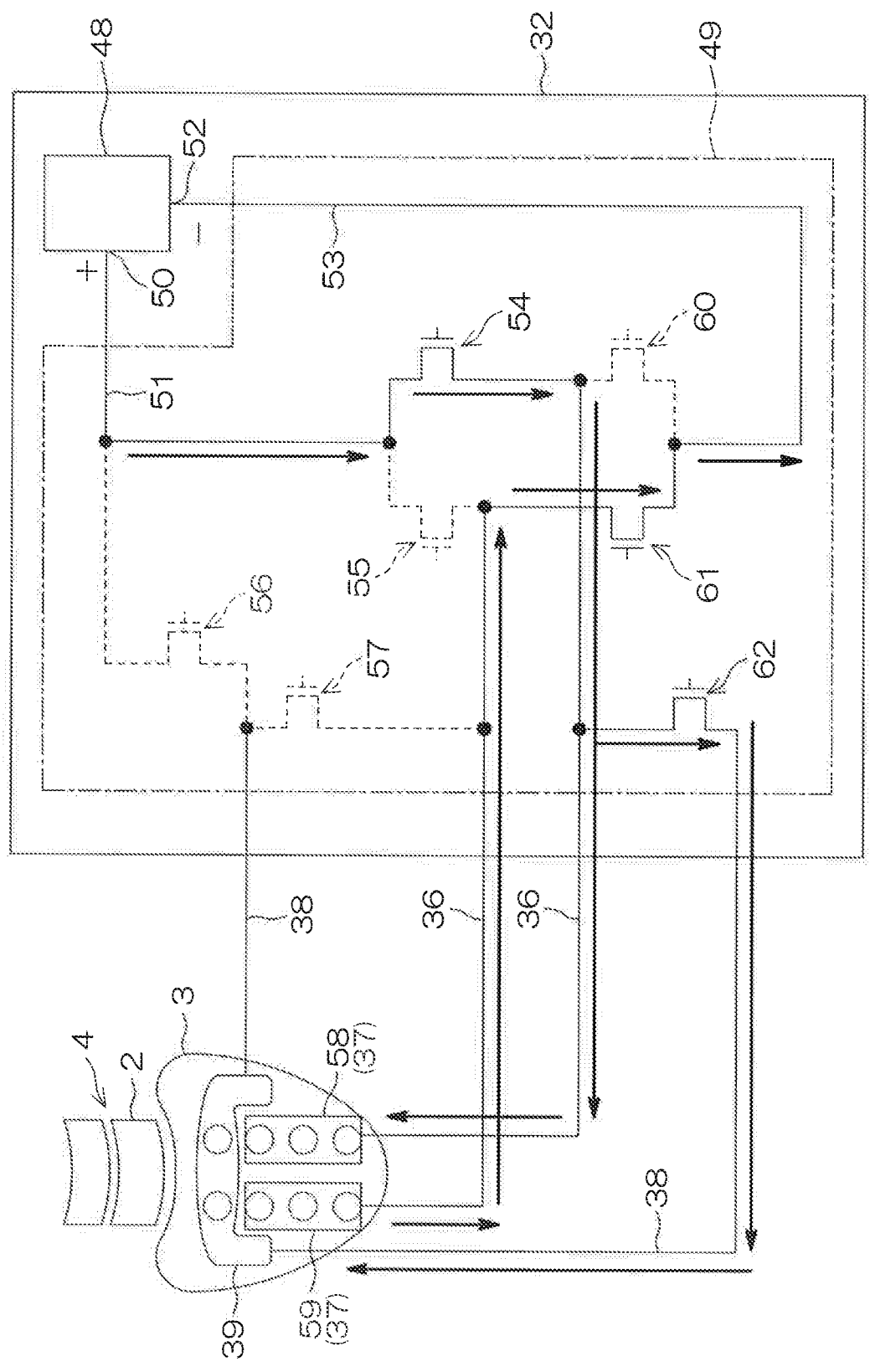
FIG. 7   ON signal when minus (-) potential is predominantly given to second stimulation electrode 59

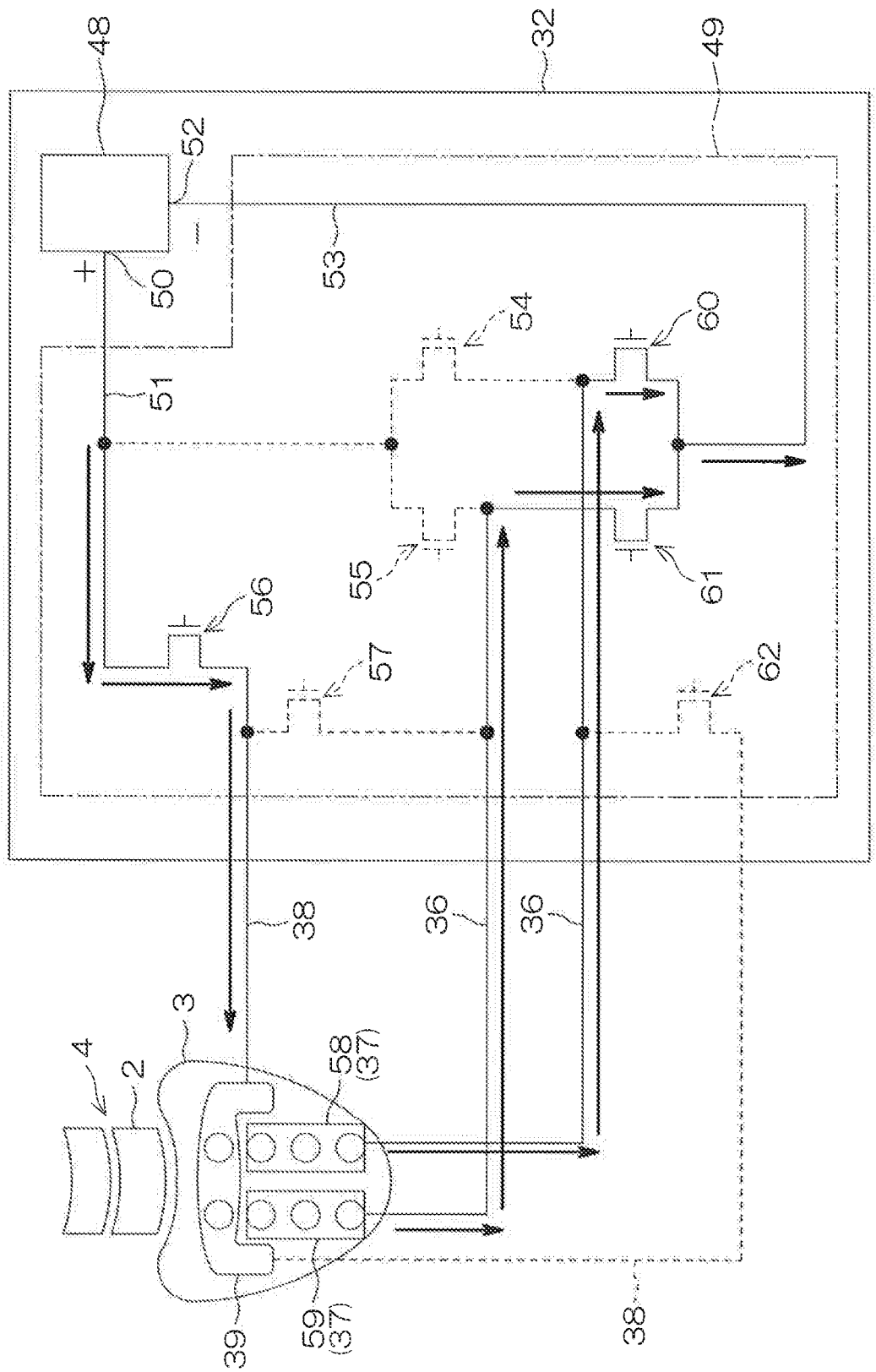

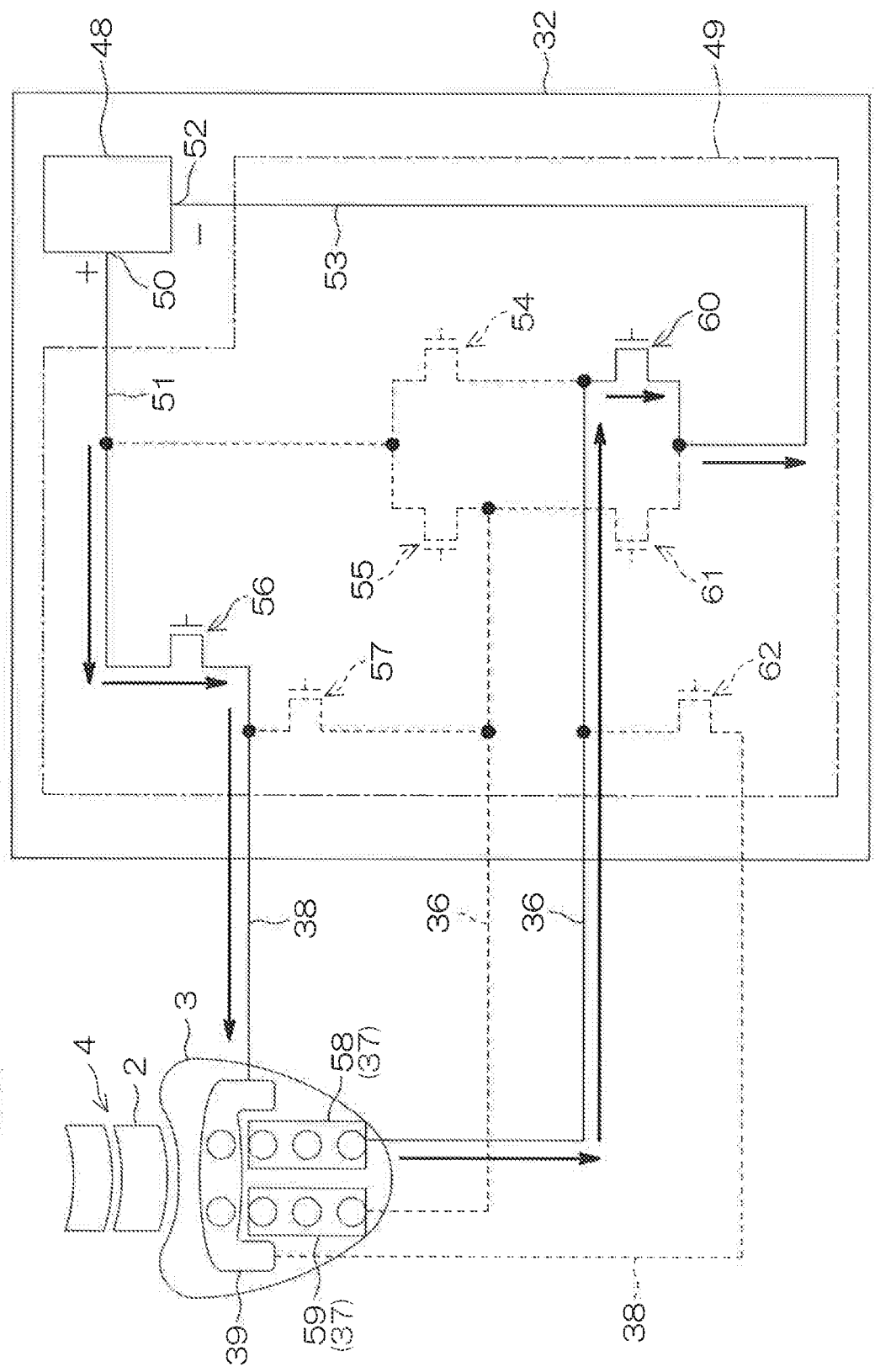

FIG. 13A (First stimulation electrode pad)
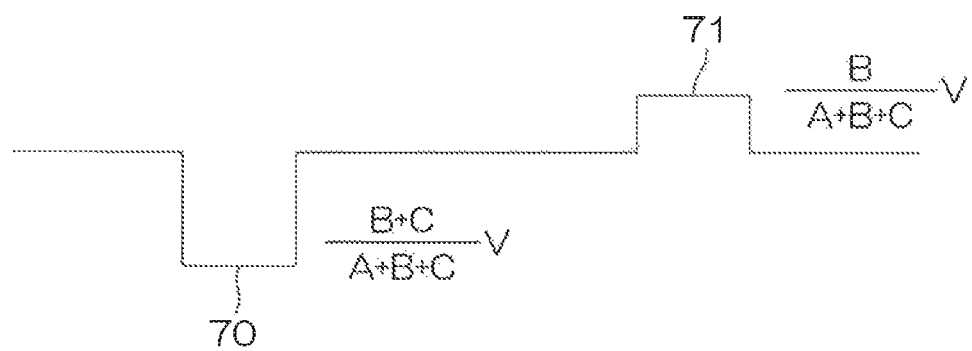
FIG. 13B (Second stimulation electrode pad)
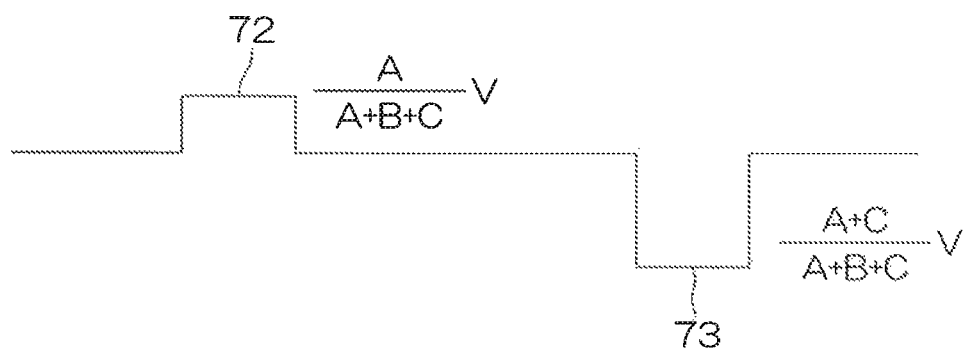
FIG. 13C (Indifferent electrode pad)
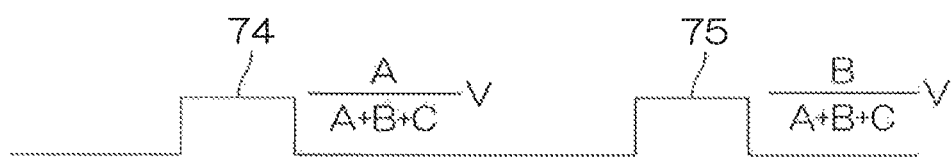

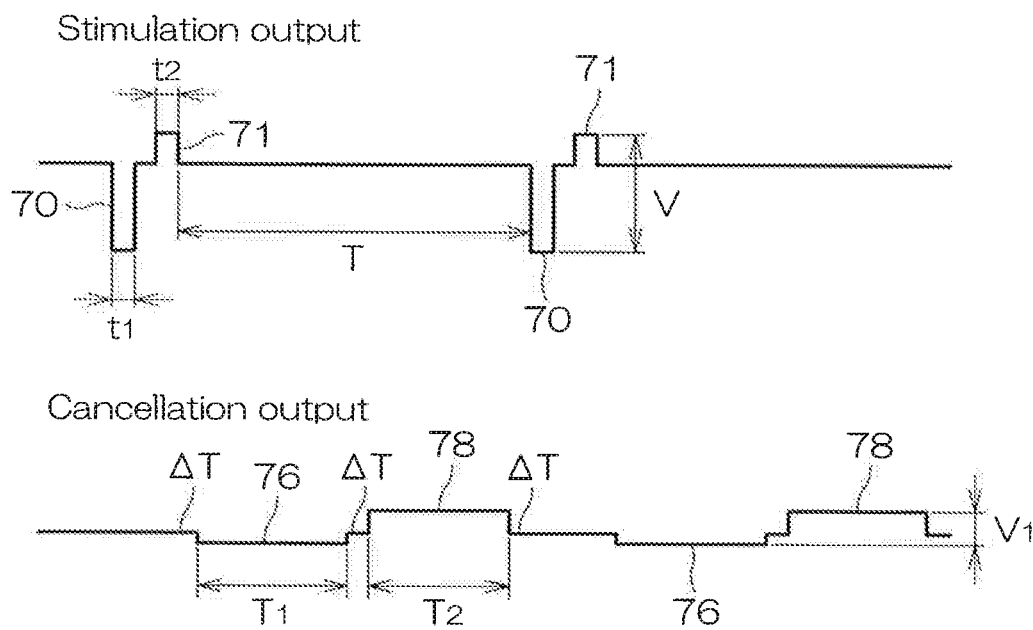
FIG. 13D (Cancellation output to first stimulation electrode pad)
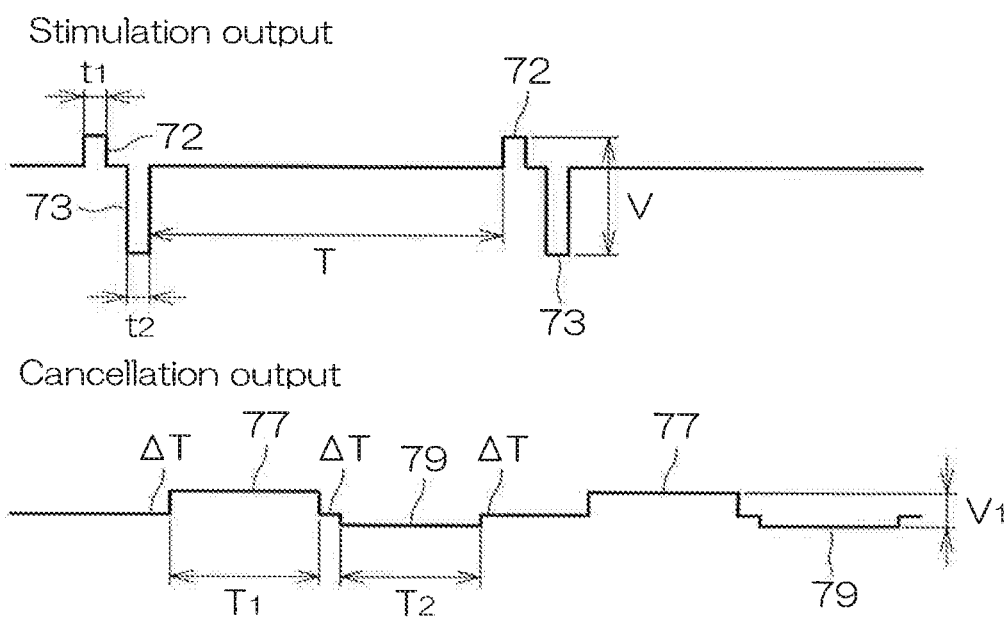
FIG. 13E (Cancellation output to second stimulation electrode pad)

FIG. 14A (First stimulation electrode pad)
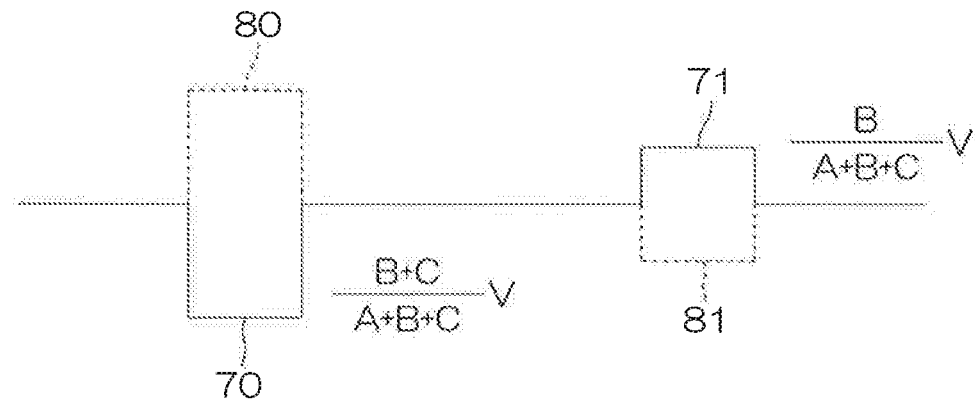
FIG. 14B (Second stimulation electrode pad)
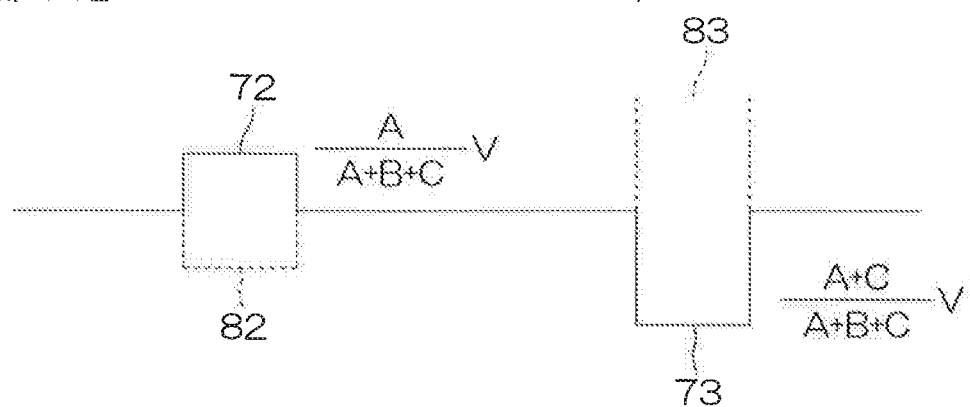
FIG. 14C (Indifferent electrode pad)
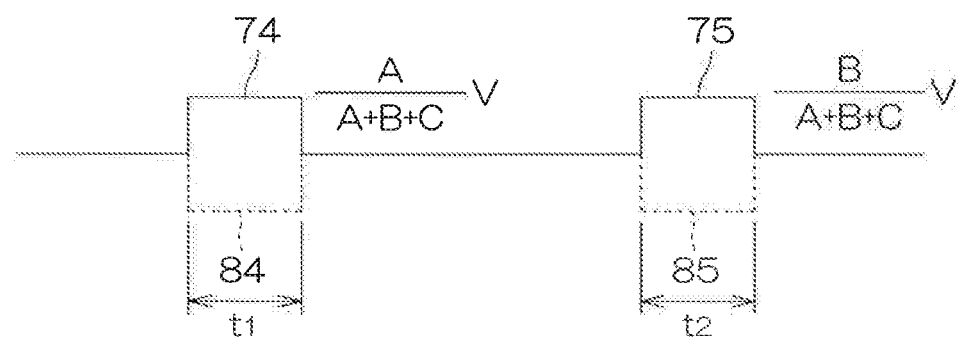

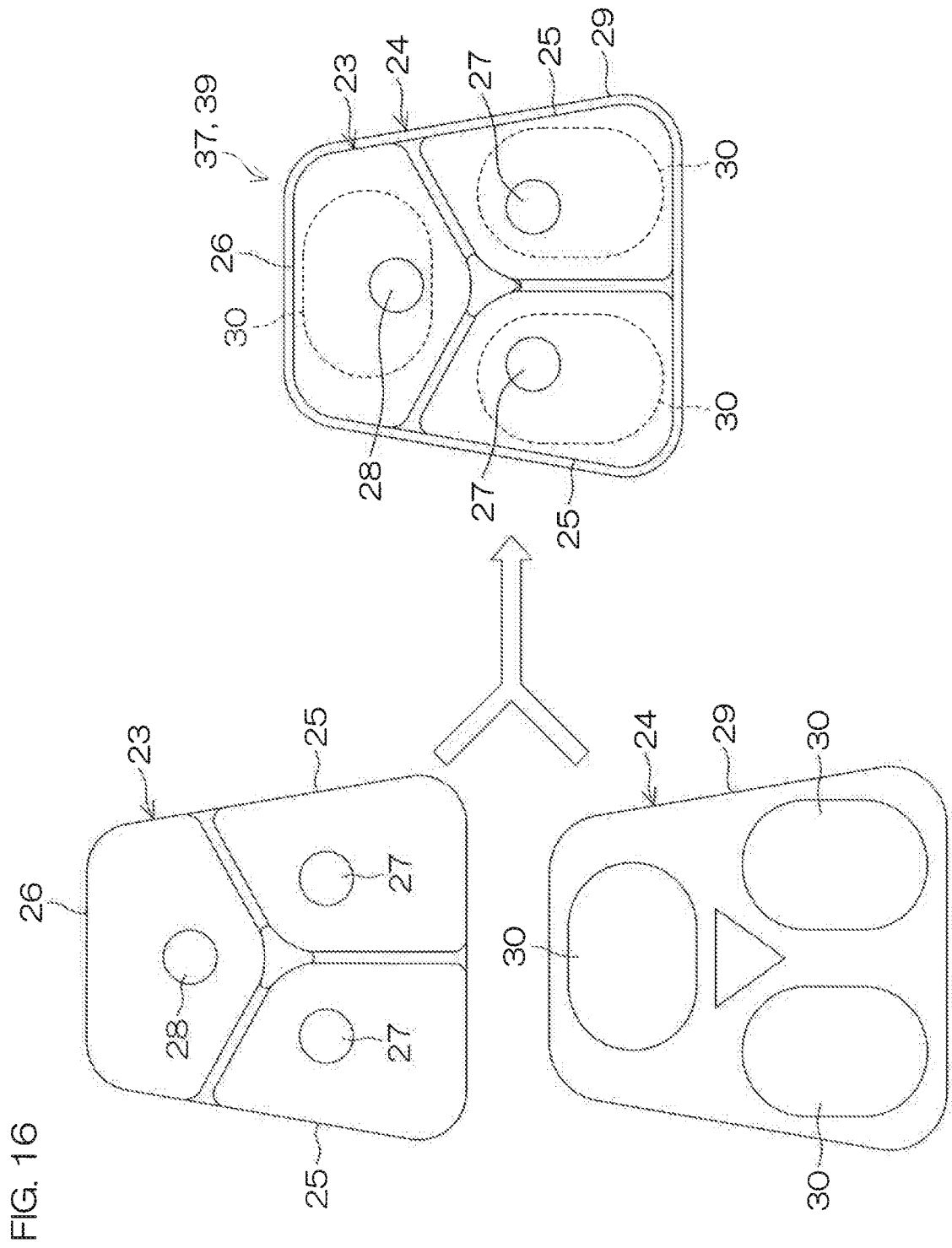

ELECTRICAL STIMULATION THERAPY INSTRUMENT

TECHNICAL FIELD

The present invention relates to a device which is used for electrical stimulation therapy.

BACKGROUND ART

As an example of a device used for electrical stimulation therapy, there has been so far proposed a device for treating a urination disorder.

For example, Patent Literature 1 has disclosed a pelvic viscera dysfunction or a pain treatment device which is provided with a CPU (central processing unit), an emergency stimulation switch connected to the CPU, a manual stimulation maximum value setting dial connected to the CPU, a stimulation frequency changeover switch, an output portion having a D/A converter, and electrodes including an indifferent electrode and a different electrode (stimulation electrode) to which an electrical stimulation is applied. In this device, to the pelvic splanchnic nerve and the pudic nerve which are a second to a fourth sacral nerve of the human body, an electrical stimulation is given to excite these nerves from the skin immediately above a second to a fourth posterior sacral foramina, and a urination disorder is treated in this manner.

CITATION LIST

Patent Literature

Patent Literature 1: Japanese Patent No. 4839457

SUMMARY OF INVENTION

Technical Problem

For example, in Patent Literature 1, the indifferent electrode is disposed at the anterior lower abdomen so that an electrical current can flow reliably from a posterior sacral foramen to an anterior sacral foramen. However, nothing has been disclosed at all about a method or others for efficiently outputting a stimulation voltage from the different electrode (stimulation electrode).

Further, in the above-described device, treatment effects will be reduced unless the stimulation electrode is attached at an appropriate position. Thus, ease in attachment of the stimulation electrode is required.

An object of the present invention is to provide an electrical stimulation treatment device which is capable of outputting a stimulation voltage efficiently as compared with a conventional device.

Another object of the present invention is to provide an electrical stimulation treatment device in which an application electrode can be attached to a stimulation site easily as compared with a conventional device.

Solution to Problem

An electrical stimulation treatment device according to one aspect of the present invention includes a pair of application electrodes which are disposed at a site of the skin of a person to be treated where an electrical stimulation is to be given and which supply an electrical stimulation signal to the skin, an indifferent electrode which is larger in area than an application electrode with a relatively larger area, of the pair of application electrodes, and which is disposed in the vicinity of the site where the electrical stimulation is to be given, and a control portion which supplies an electrical signal to the pair of application electrodes and the indifferent electrode, in which the control portion executes any one of the following processing, that is, (1) the stimulation signal is output from one of the pair of application electrodes with respect to a reference potential set to an average potential of the other of the pair of application electrodes and the indifferent electrode, (2) the stimulation signal is output from both of the pair of application electrodes with respect to a reference potential set to the indifferent electrode, or (3) the stimulation signal is output from one of the pair of application electrodes with respect to a reference potential set to the indifferent electrode.

In the electrical stimulation treatment device according to one aspect of the present invention, the pair of application electrodes may be mutually equal in area and the indifferent electrode may have an area which is 0.25 to 10 times larger than each of the application electrodes.

In the electric stimulation treatment device according to one aspect of the present invention, the control portion executes the stimulation signal output processing of (1), (2) or (3) by supplying an electric signal which generates a predetermined pulse pattern, and the control portion may also supply, between the adjacent pulses, to the indifferent electrode an electric signal which generates a negative-side voltage pulse with respect to the reference potential.

In the electric stimulation treatment device according to one aspect of the present invention, the pair of application electrodes include a first stimulation electrode and a second stimulation electrode, and the control portion controls the output in an alternating pulse pattern which alternately generates a first pattern and a second pattern, in the first pattern, a voltage pulse being generated so that the first stimulation electrode will be a negative side and the second stimulation electrode and the indifferent electrode will be a positive side with respect to a reference potential set to an average potential of the second stimulation electrode and the indifferent electrode, and in the second pattern, a voltage pulse being generated so that the second stimulation electrode will be a negative side and the first stimulation electrode and the indifferent electrode will be a positive side with respect to a reference potential set to an average potential of the first stimulation electrode and the indifferent electrode. Further, the control portion may apply a voltage to the first stimulation electrode, the second stimulation electrode and the indifferent electrode so as to generate, between the second pattern and the first pattern which is a next cycle, a corrected pulse in which a pulse of each of the first stimulation electrode, the second stimulation electrode and the indifferent electrode in the first pattern and a pulse of each of the first stimulation electrode, the second stimulation electrode and the indifferent electrode in the second pattern are inverted in terms of a polarity of each of them.

In the electric stimulation treatment device according to one aspect of the present invention, the control portion executes the stimulation signal output processing of (1), (2) or (3) by supplying an electric signal which generates a predetermined pulse pattern, and the control portion may also supply, after the stimulation signal processing, to the pair of application electrodes and the indifferent electrode an electric signal so as to generate a pulse pattern which is inverted in positive voltage and negative voltage to the pulse pattern.

The electric stimulation treatment device according to one aspect of the present invention may include an operation portion by which a user can select any one of the processing to be used among the stimulation signal output processing of (1), (2) and (3) of the control portion.

In the electric stimulation treatment device according to one aspect of the present invention, the pair of application electrodes may include a pair of application electrodes which are disposed side by side at the back of a sacrum of a person to be treated to supply an electric stimulation signal from the back of the sacrum, and the indifferent electrode may include an indifferent electrode which is disposed in the vicinity of the pair of application electrodes at the back of the sacrum.

An electric stimulation treatment device according to another aspect of the present invention includes a main body of a treatment device, a wiring portion which is connected to the main body of the treatment device, a pair of application electrodes which are attached to the wiring portion and disposed at a site of the skin of a person to be treated where an electric stimulation is to be given and which supply an electric stimulation signal to the skin, and a magnetic connection portion which magnetically connects the wiring portion with the pair of application electrodes.

In the electric stimulation treatment device according to another aspect of the present invention, the pair of application electrodes may include a pair of application electrodes which are disposed side by side at the back of the sacrum of a person to be treated to supply an electric stimulation signal from the back of the sacrum.

Advantageous Effects of Invention

In the electric stimulation treatment device according to one aspect of the present invention, for example, in the processing of (1), one of the pair of application electrodes is a stimulation electrode and the other of the pair of application electrodes and the indifferent electrode are a reference electrode. A voltage is applied between the reference electrode and the stimulation electrode so that the reference electrode will be a positive side (plus side) and the stimulation electrode will be a negative side (minus side). Thereby, directly under the reference electrode (anode), within a time during which a voltage is applied, as compared with before application of a voltage, a positive potential is developed. Negative ions are accumulated inside a cell wall of a nerve cell present directly under the reference electrode (anode) to suppress excitement of the nerve. On the other hand, directly under the stimulation electrode (cathode), as compared with before application of the voltage, a negative potential is developed. Positive ions are accumulated inside the cell wall of the nerve cell present directly under the stimulation electrode (cathode) to cause excitement of the nerve. Thus, a first capacitor which includes the reference electrode (anode) and a skin region in contact therewith as a counter electrode and a second capacitor which includes the stimulation electrode (cathode) and a skin region in contact therewith as a counter electrode are provided. The first capacitor and the second capacitor are connected in series. Therefore, an applied voltage is distributed to the first capacitor and the second capacitor in inverse proportion to a static capacitance of each capacitor. Specifically, when an applied voltage is given as V and a static capacitance of the first capacitor and that of the second capacitor are respectively given as a static capacitance $C1$ and a static capacitance $C2$, a voltage of $V \times (C2/(C1+C2))$ is applied to a positive side of the first capacitor and a voltage of $V \times (C1/(C1+C2))$ is applied to a negative side of the second capacitor. The static capacitances $C1$ and $C2$ are increased in proportion to an area of the electrode. Therefore, as described in the invention of the application concerned, the reference electrode which is given as a reference potential is made larger in area than the stimulation electrode, by which a negative-side voltage applied to the stimulation electrode can be made relatively larger than a positive-side voltage applied to the reference electrode. As a result, the negative-side potential which is effective in exciting the nerve is increased and the positive-side potential which is unnecessary in exciting the nerve is decreased, thus making it possible to output a stimulation voltage more efficiently than a conventional device.

In the electric stimulation treatment device according to another aspect of the present invention, the application electrode is connected with the wiring portion of the device by way of the magnetic connection portion. Therefore, the application electrode can be easily detached from the wiring portion. The application electrode can be attached to a stimulation site in separation from the main body of the treatment device or the wiring portion and, therefore, the application electrode can be attached more easily than a conventional device. Further, after attachment of the application electrode to the stimulation site, a magnetic connection portion on the wiring portion side is brought close to a magnetic connection portion on the application electrode side, by which these portions can be attracted to each other and connected magnetically and connection works can be made easier.

BRIEF DESCRIPTION OF DRAWINGS

FIG. 2 is a rear view of the human body for describing innervation of urination.

FIG. 3B is a drawing for describing a mechanism of urination.

FIG. 6 is a drawing which shows a flow (first pattern) of a stimulation signal of the urination disorder treatment device.

FIG. 7 is a drawing which shows a flow (second pattern) of a stimulation signal of the urination disorder treatment device.

FIG. 8 is a drawing which shows a flow (third pattern) of a stimulation signal of the urination disorder treatment device.

FIG. 9 is a drawing which shows a flow (fourth pattern) of a stimulation signal of the urination disorder treatment device.

FIG. 13A is a drawing which shows a pulse pattern of a first stimulation electrode pad.

FIG. 13B is a drawing which shows a pulse pattern of a second stimulation electrode pad.

FIG. 13C is a drawing which shows a pulse pattern of an indifferent electrode pad.

FIG. 13D is a drawing which shows cancellation output to the first stimulation electrode pad.

FIG. 13E is a drawing which shows cancellation output to the second stimulation electrode pad.

FIG. 14A is a drawing which shows a pulse pattern of the first stimulation electrode pad.

FIG. 14B is a drawing which shows a pulse pattern of the second stimulation electrode pad.

FIG. 14C is a drawing which shows a pulse pattern of the indifferent electrode pad.

FIG. 16 is a drawing which describes a variation of the shape of the electrode pad.

DESCRIPTION OF EMBODIMENTS

Hereinafter, modes of executing the present invention will be described in detail with reference to attached drawings.

Figure 1:
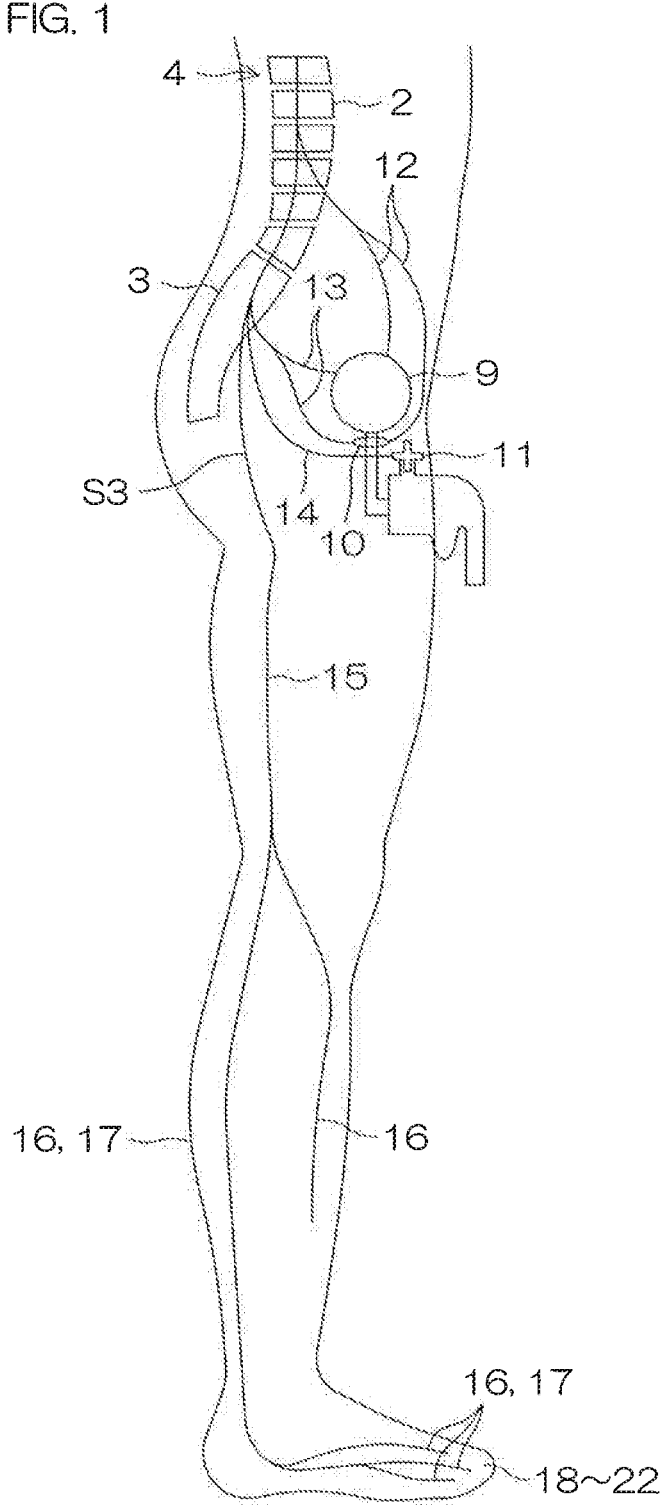
FIG. 1 is a side sectional view of the human body for describing innervation of urination.
Figure 3A:
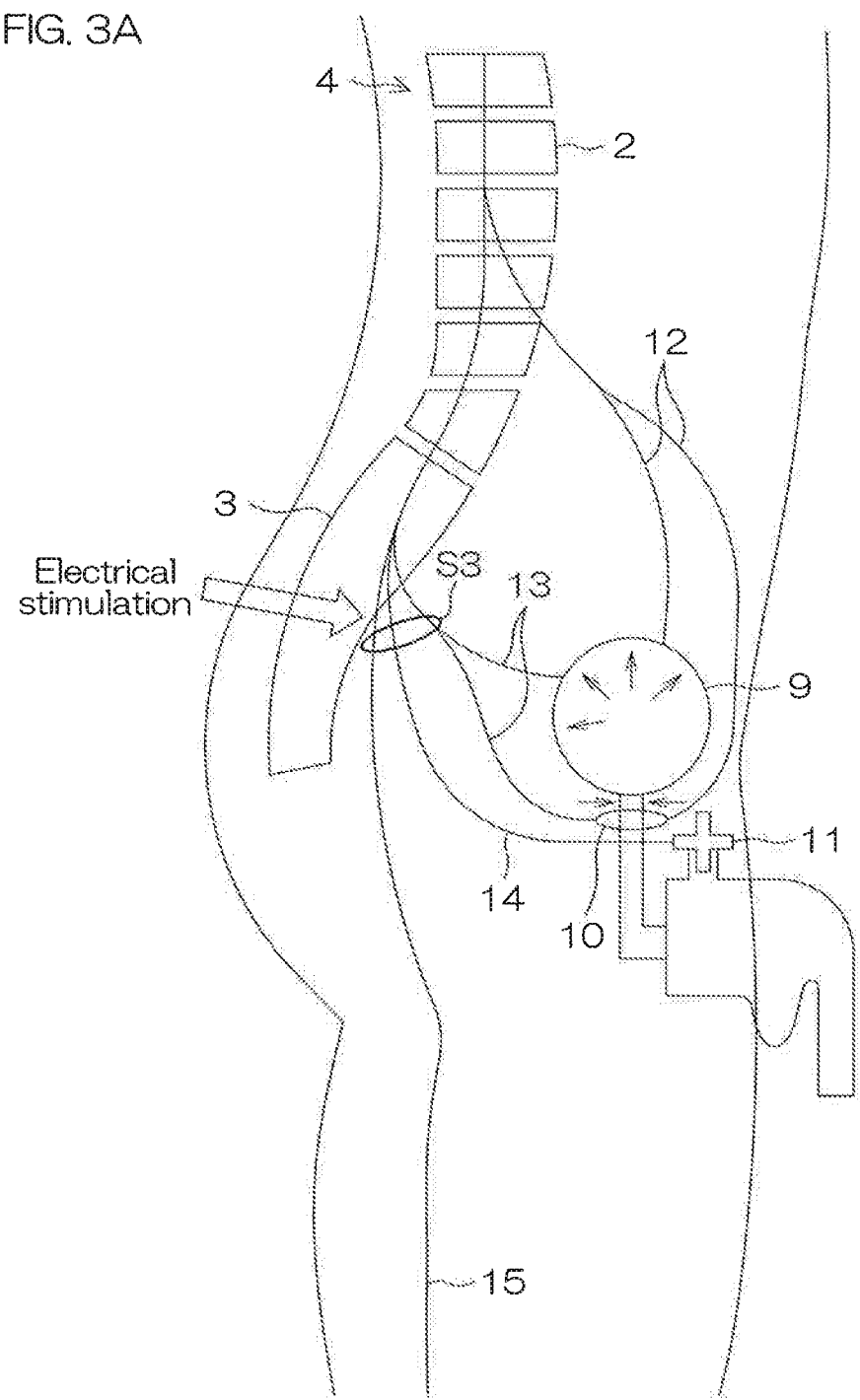
FIG. 3A is a drawing for describing a mechanism of urination.

FIG. 1 is a side sectional view of a human body 1 for describing innervation of urination. FIG. 2 is a rear view of the human body 1 which describes innervation of urination. FIG. 3A and FIG. 3B are each a drawing which describes a mechanism of urination. In FIG. 1 to FIGS. 3A and 3B, of various sites of the human body 1, there are shown only sites which are necessary for describing treatment by using a urination disorder treatment device 31 according to a preferred embodiment of the present invention, with a description of other sites being omitted here.

The human body 1 has a vertebral column 4 which includes a lumbar vertebra 2, a sacral bone 3 and others. The sacral bone 3 assumes a substantially inverted triangular shape, normally having four foramina on both sides symmetrically, from above, a first sacral foramen 5, a second sacral foramen 6, a third sacral foramen 7, and a fourth sacral foramen 8.

Further, the human body 1 has a bladder 9, an internal urethral sphincter 10 and an external urethral sphincter 11 as sites (organs and muscles) involved in collecting and discharging urine. These sites of 9 to 11 are neurologically controlled to collect and discharge urine in the human body 1.

In the human body 1, nerves mainly contributing to collection and discharge of urine are a hypogastric nerve (sympathetic nerve) 12, a pelvic nerve (parasympathetic nerve) 13 and a pudic nerve (somatic nerve) 14.

The hypogastric nerve 12 contributes to suppression of urination (urine collection) and is connected to the bladder 9 and the internal urethral sphincter 10. The pelvic nerve 13 contributes to the initiation of urination and connected to the bladder 9 and the internal urethral sphincter 10. The pudic nerve 14 is connected to the external urethral sphincter 11.

As shown in FIG. 3A, in the human body 1, first, the bladder 9 (detrusor muscle) is relaxed by a signal from the hypogastric nerve 12, by which urine can be easily collected in the bladder 9 and the internal urethral sphincter 10 is also contracted. Thereby, urine is prevented from being discharged but collected inside the bladder 9. On the other hand, as shown in FIG. 3B, the bladder 9 (detrusor muscle) is contracted by a signal from the pelvic nerve 13, and the internal urethral sphincter 10 is also relaxed. Thereby, urine is discharged outside the bladder 9. Then, the external urethral sphincter 11 as a voluntary muscle is relaxed by a command from the brain of the human body 1 (one's own volition) by way of the pudic nerve 14 which is a somatic nerve, and an abdominal muscle pressure is applied to discharge urine.

As described above, if the hypogastric nerve 12 and the pelvic nerve 13 are both normally engaged in activity to appropriately contract and relax the bladder 9 and the internal urethral sphincter 10, urine is collected or discharged normally. However, for example, when the hypogastric nerve 12 is activated at a lower level or the pelvic nerve 13 is activated excessively, the bladder 9 is more likely to contract and the internal urethral sphincter 10 is more likely to relax. As a result, urine is more easily collected in the bladder 9, which may trigger onset of a urination disorder such as a urine collection failure (overactive bladder).

Thus, in the preferred embodiment, as shown in FIG. 3A, an electrical stimulation signal is given to the skin on the sacral bone 3 from the back of the sacral bone 3, thereby stimulating the sacral plexus. More specifically, as shown in FIG. 2, there are stimulated a first sacral nerve S1 which passes through the first sacral foramen 5, a second sacral nerve S2 which passes through the second sacral foramen 6, a third sacral nerve S3 which passes through the third sacral foramen 7 and a fourth sacral nerve S4 which passes through the fourth sacral foramen 8. Thereby, for example, as shown in FIG. 3A, the third sacral nerve S3 is stimulated to suppress innervation which causes the bladder 9 to be contracted by the pelvic nerve 13. Further, this electrical stimulation is also sent to the hypogastric nerve 12, thereby accelerating innervation which allows the bladder 9 to be relaxed by the hypogastric nerve 12. As a result, suppression of the pelvic nerve 13 is well-balanced with acceleration of the hypogastric nerve 12, by which the bladder 9 is appropriately relaxed to improve an overactive bladder.

Next, the above-described electrical stimulation is also transmitted to the nerves present at sites other than the buttocks and peripheries thereof at which the sacral plexus is found. For example, as shown in FIG. 2, some of the third sacral nerves S3 partially descend the femur as an ischiadic nerve 15 and finally are divided into a peroneal nerve 16 and a tibial nerve 17. The peroneal nerve 16 and the tibial nerve 17 extend up to toes of the human body 1 (a first toe 18 (big toe), a second toe 19, a third toe 20, a fourth toe 21 and a fifth toe 22 (little toe)) as terminal portions of the ischiadic nerve 15. That is, the peroneal nerve 16 and the tibial nerve 17 of the toes 18 to 22 are connected by way of the ischiadic nerve 15 to the hypogastric nerve 12, the pelvic nerve 13 and the pudic nerve 14.

Next, a description will be given of a configuration and operation of a urination disorder treatment device 31 as an example of an electrical stimulation treatment device according to the first preferred embodiment of the present invention.

First Preferred Embodiment

Figure 4:
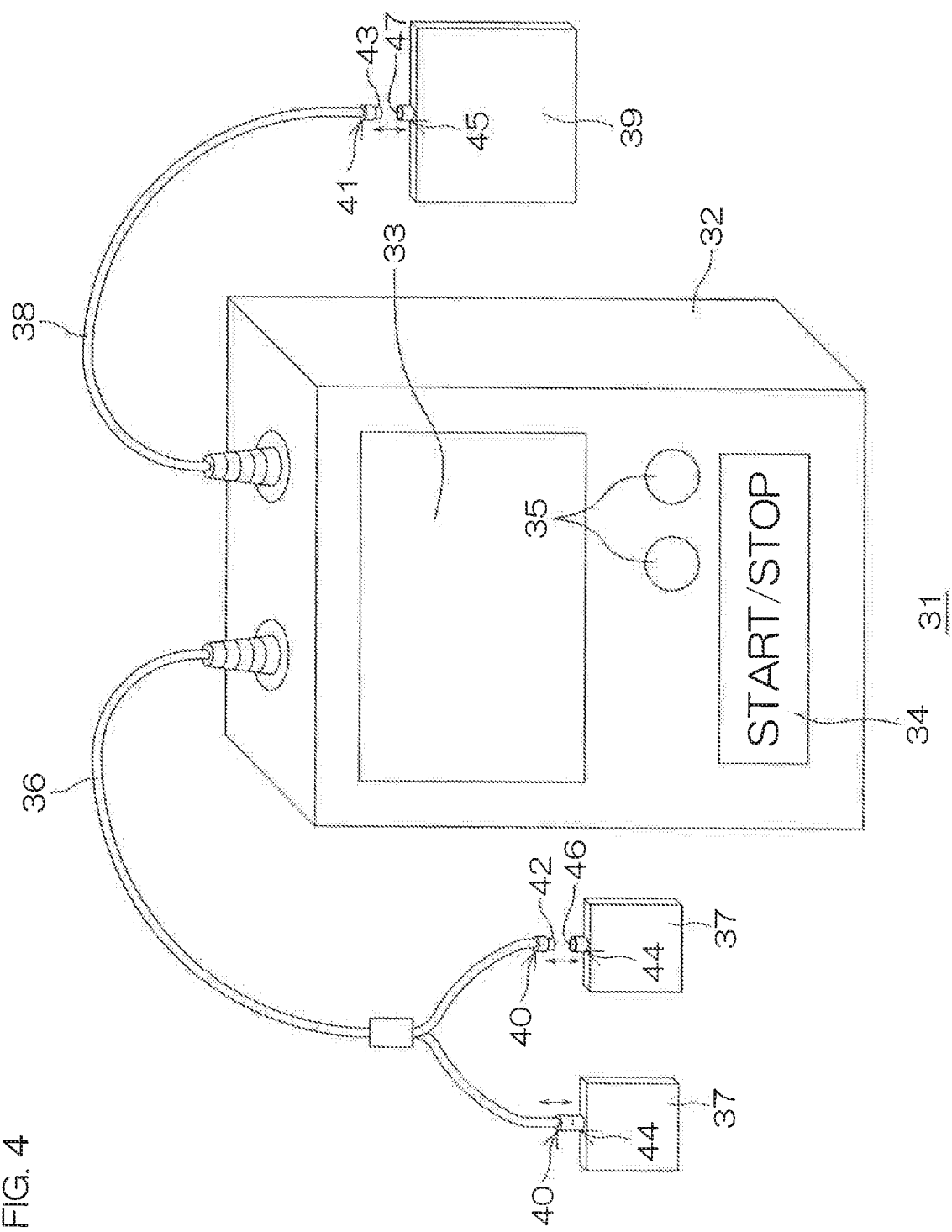
FIG. 4 is a schematic view of a urination disorder treatment device according to a preferred embodiment of the present invention.

FIG. 4 is a schematic view of a urination disorder treatment device 31 according to the first preferred embodiment of the present invention.

The urination disorder treatment device 31 is physically arranged to have a body 32 which is an example of a main body of the treatment device of the present invention, a monitor 33 placed on a front surface of the body 32, a start/stop button 34 and a plurality of operation buttons 35, 35 placed below the monitor 33, a pair of body-surface electrode pads 37 which are connected, as an example of the application electrodes of the present invention, to the body 32 by way of an insulation cable 36, as an example of the wiring portion of the present invention, and an indifferent electrode pad 39 which is connected, as an example of the indifferent electrode of the present invention, to the body 32 byway of an insulation cable 38.

The body 32 may be, for example, a plastic-made case. Further, although not shown in the drawing, at the back of the body 32, there may be provided a removable back lid for housing a battery for a power source of the urination disorder treatment device 31. The power source of the urination disorder treatment device 31 may not necessarily be a battery but may be obtained, for example, from an electrical outlet by way of an AC adaptor. Alternatively, the battery may be used together with the outlet.

The monitor 33 may be, for example, a black-and-white or color liquid crystal monitor. On the monitor 33, there can be displayed, for example, a pulse waveform and a frequency of an electrical stimulation signal by the body-surface electrode pad 37, an electrocardiographic waveform and a heart rate of a person to be treated, an error message and others. Thereby, the person to be treated is able to easily know the operating state of the urination disorder treatment device 31.

The operation button 35 may have various functions depending on a type of the urination disorder treatment device 31. For example, as a memory function of the urination disorder treatment device 31, a treatment menu including a width of a pulse wave (pulse width), a frequency of a stimulation signal, suitable for each of a plurality of persons to be treated is stored in the urination disorder treatment device 31, and the button, etc., that is operated in reading a treatment menu may be provided. It may also be a button for deciding selection of a voltage application pattern, of the voltage application patterns shown in FIG. 6 to FIG. 9.

The insulation cable 36 and the insulation cable 38 are arranged, for example, with a conducting wire covered with a protective insulation film, and they are provided at the respective ends of the body-surface electrode pad 37 and the indifferent electrode pad 39 having a magnet adaptor 40 and a magnet adaptor 41, as an example of the magnetic connection portion of the present invention. The magnet adaptor 40 and the magnet adaptor 41 are respectively provided with terminals (male terminals) 42, 43 which are electrically connected to the conducting wires inside the insulation cable 36 and the insulation cable 38.

As the body-surface electrode pads 37 and the indifferent electrode pad 39, for example, any known adhesive gel pad, etc., can be used. Further, the indifferent electrode pad 39 is larger in area than a body-surface electrode pad 37 with a relatively larger area, of the pair of body-surface electrode pads 37. The area of each of the body-surface electrode pad 37 and the indifferent electrode pad 39 can be defined, for example, as an area of a surface in contact with the skin of the human body 1 in the body-surface electrode pad 37 and the indifferent electrode pad 39. In the preferred embodiment, the pair of body-surface electrode pads 37 are formed in the same shape as each other to have the same area. The indifferent electrode pad 39 is 0.25 to 10 times larger in area than each of the body-surface electrode pads 37. As a matter of course, one of the pair of body-surface electrode pads 37 may be relatively larger in area than the other.

As an example of the magnetic connection portion of the present invention, a magnet port 44 and a magnet port 45 are provided respectively at a periphery of the pair of body-surface electrode pads 37 and that of the indifferent electrode pad 39. The magnet port 44 and the magnet port 45 are respectively provided with terminals (female terminals) 46, 47 connected electrically to the conducting wires inside the body-surface electrode pad 37 and the indifferent electrode pad 39.

The female terminal 46 and the female terminal 47 are formed in such a shape that the male terminal 42 and the male terminal 43 can be respectively fitted. Thereby, a user is able to bring close the male terminal 42 and the male terminal 43 respectively to the female terminal 46 and the female terminal 47, thus making it possible to connect them by being magnetically attracted to each other. In FIG. 4, the pair of body-surface electrode pads 37 are shown in a state that the magnet adaptor 40 is connected to the magnet port 44 on the left side in the space of the drawing and the magnet adaptor 40 is kept apart from the magnet port 44 on the right side in the space.

Figure 5:
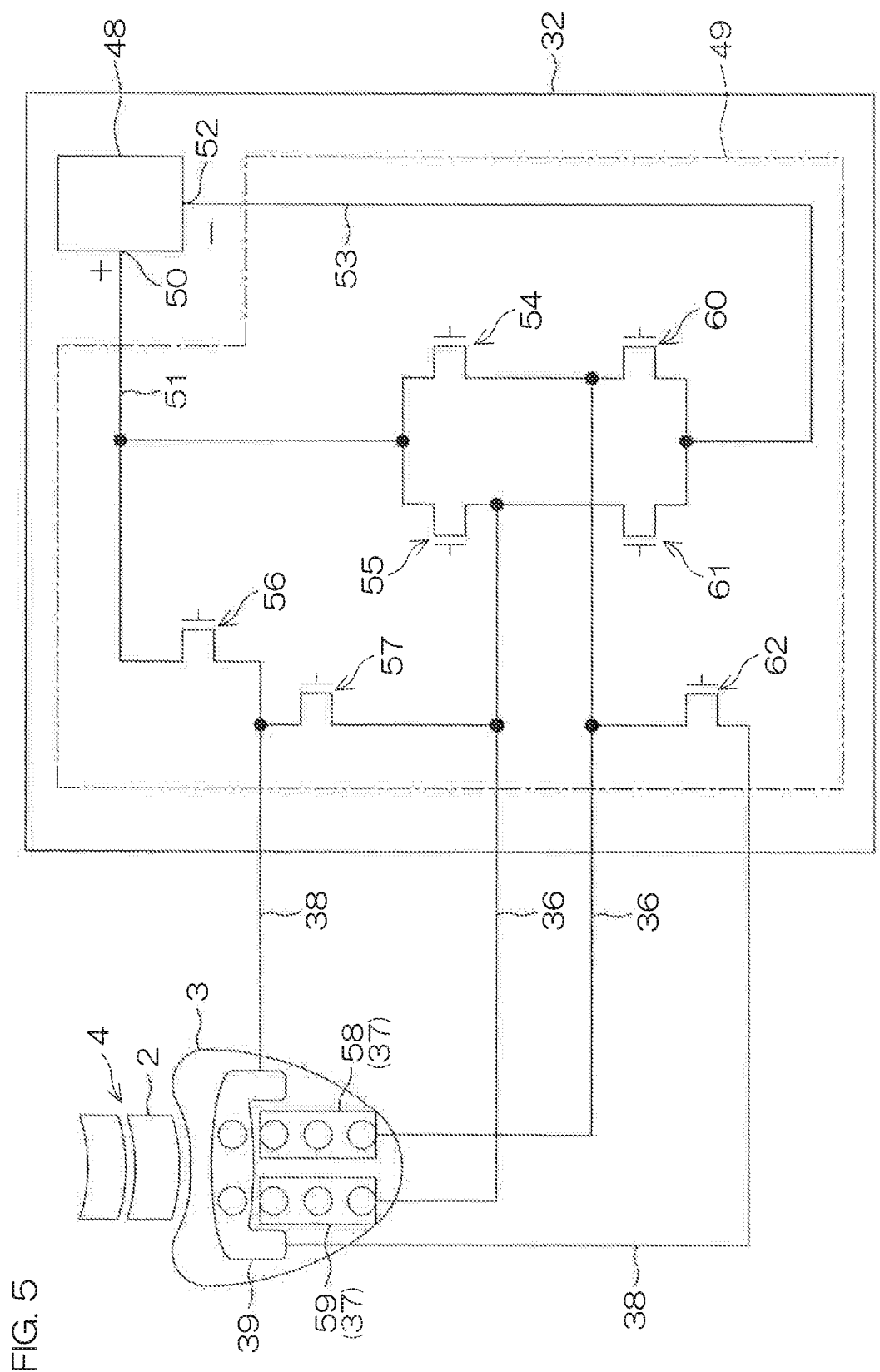
FIG. 5 is a drawing which shows a position at which an electrode pad of the urination disorder treatment device is attached and an electric configuration of the urination disorder treatment device.
Figure 10A:
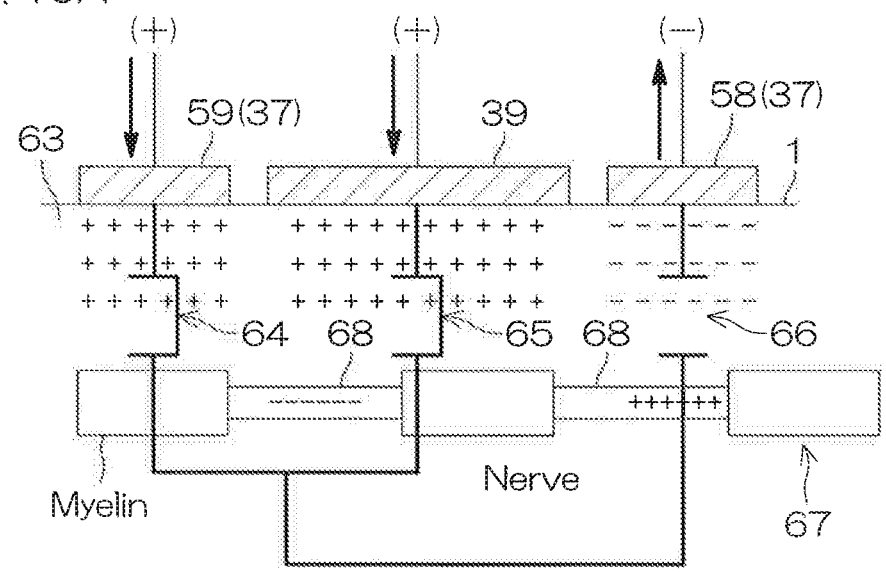
FIG. 10A is a drawing which shows distribution of a charge upon application of an electric stimulation (preferred embodiment of the present invention).
Figure 10B:
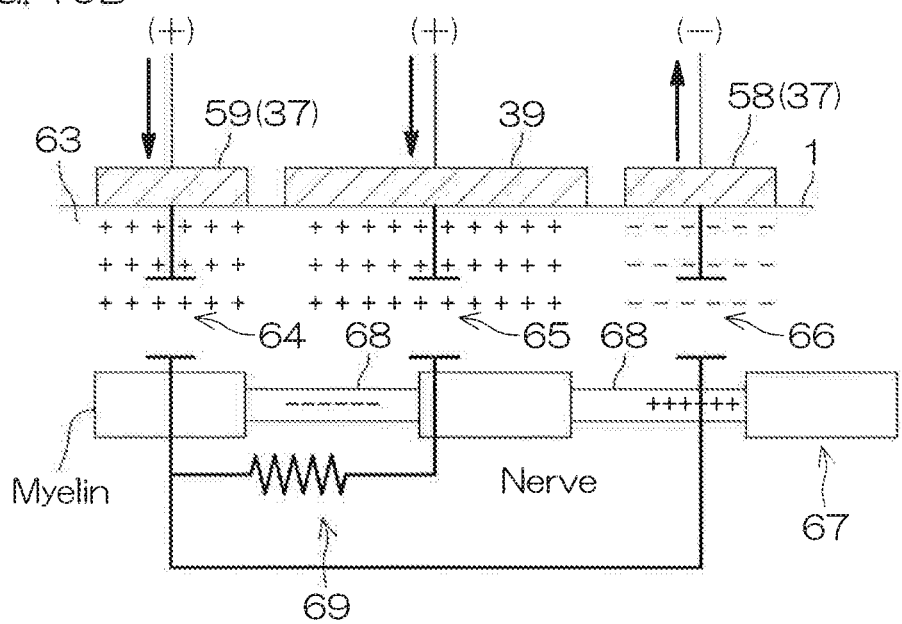
FIG. 10B is a drawing which shows distribution of a charge upon application of an electric stimulation (reference example).
Figure 11A:
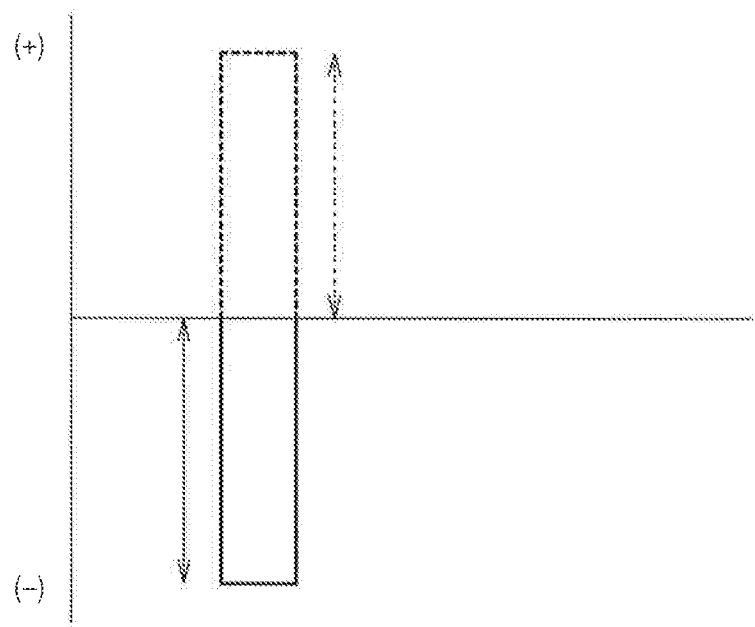
FIG. 11A is a drawing which shows a pulse waveform of a urination disorder treatment device according to the reference example.
Figure 11B:
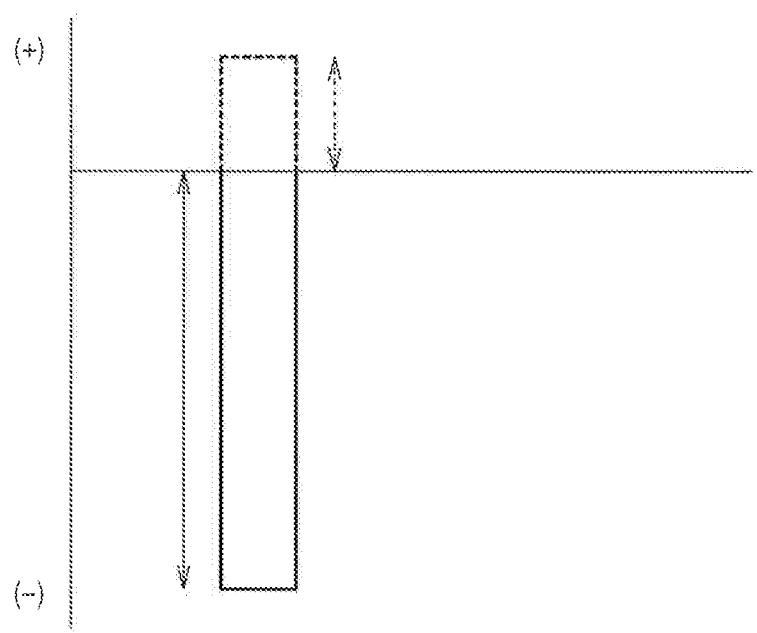
FIG. 11B is a drawing which shows a pulse waveform of the urination disorder treatment device according to a preferred embodiment of the present invention.

FIG. 5 is a drawing which shows positions at which the electrode pads 37, 39 of the urination disorder treatment device 31 are attached and an electric configuration of the urination disorder treatment device 31. FIG. 6 to FIG. 9 are each a drawing which shows a flow of a stimulation signal of the urination disorder treatment device 31 (first to fourth pattern). FIG. 10A and FIG. 10B are each a drawing which shows distribution of a charge when an electric stimulation is given. FIG. 11A is a drawing which shows a pulse waveform of a urination disorder treatment device according to the reference example. FIG. 11B is a drawing which shows a pulse waveform of the urination disorder treatment device 31.

The urination disorder treatment device 31 is electrically arranged to have a control portion 48 and a circuit portion 49 electrically connected to the control portion 48 inside the body 32.

The control portion 48 may be arranged with a microcomputer including, for example, a CPU, memories such as ROM and RAM and a timer as well as a booster circuit which generates a stimulation voltage.

The circuit portion 49 is composed of, for example, a semiconductor integrated circuit (IC) chip, and includes, as a wiring inside the chip, a plus side wiring 51 connected to a plus side terminal 50 of the control portion 48 and a minus side wiring 53 of a minus side terminal 52 of the control portion 48.

The circuit portion 49 is also provided with a plurality of switch portions 54 to 57 for controlling a voltage on the plus side. The switch portions 54 to 57 may be composed of, for example, a semiconductor switch (MOSFET, etc.,) which is turned on by application of a gate voltage and a semiconductor relay. The switch portion 54 is placed at a midpoint of a circuit which electrically connects one of the pair of body-surface electrode pads 37 (a first stimulation electrode pad 58) with the plus side wiring 51. The switch portion 55 is placed at a midpoint of a circuit which electrically connects the other of the pair of body-surface electrode pads 37 (a second stimulation electrode pad 59) with the plus side wiring 51. The switch portion 56 is placed at a midpoint of a circuit which electrically connects the indifferent electrode pad 39 with the plus side wiring 51. The switch portion 57 is placed between the circuit of the second stimulation electrode pad 59 and the circuit of the indifferent electrode pad 39.

The circuit portion 49 is also provided with a plurality of switch portions 60 to 62 for controlling a voltage on the minus side. The switch portions 60 to 62 may be composed of, for example, a semiconductor switch (MOSFET, etc.,) which is turned on by application of a gate voltage and a semiconductor relay. The switch portion 60 is placed at a midpoint of a circuit which electrically connects the first stimulation electrode pad 58 with the minus side wiring 53. The switch portion 61 is placed at a midpoint of a circuit which electrically connects the second stimulation electrode pad 59 with the minus side wiring 53. The switch portion 62 is placed at a midpoint of a circuit which electrically connects the indifferent electrode pad 39 with the minus side wiring 53.

Then, in using the urination disorder treatment device 31, for example, a person to be treated at first attaches the pair of body-surface electrode pads 37 (the first stimulation electrode pad 58 and the second stimulation electrode pad 59) to the skin directly above the back of the sacral bone 3 in a state that the magnet adaptor 40 and the magnet adaptor 41 are separated from the magnet port 44 and the magnet port 45. Then, the person to be treated attaches the indifferent electrode pad 39 in the vicinity of the pair of body-surface electrode pads 37. Specifically, the pair of body-surface electrode pads 37 may be disposed side by side at the back of the sacral bone 3, with an interval kept, and the indifferent electrode pad 39 may be disposed in the upper vicinity of the pair of body-surface electrode pads 37. In this instance, since the pair of body-surface electrode pads 37 and the indifferent electrode pad 39 are separated from the insulation cables 36, 38, it is not necessary to move the main body of the urination disorder treatment device 31 together, although the pair of body-surface electrode pads 37 and the indifferent electrode pad 39 are located at the back of the person to be treated. Thus, it is possible to easily attach the pair of body-surface electrode pads 37 and the indifferent electrode pad 39.

After attachment of the pair of body-surface electrode pads 37 and the indifferent electrode pad 39, the person to be treated brings the magnet adaptors 40, 41 of the insulation cables 36, 38 close to the magnet ports 44, 45 of the pair of body-surface electrode pads 37 and the indifferent electrode pad 39 and connects them by magnetically attracting them to each other. As described above, the magnet adaptors 40, 41 of the insulation cables 36, 38 can be guided magnetically to connect them quite easily.

Then, the person to be treated selects their own suitable treatment menu, by using the operation button 35 and pushes the start/stop button 34. Thereby, an electric stimulation signal is output from the body-surface electrode pad 37 to stimulate the third sacral nerve S3, thus making it possible to start the treatment by the urination disorder treatment device 31. Conditions of the stimulation signal (output pulse) may be, for example, a pulse width of 1 μs (second) to 500 μs (second) and a pulse frequency of 1 Hz to 50 Hz.

The stimulation signal is generated by application of an alternating pulse voltage to a reference potential. Therefore, there is a case that the stimulation signal (stimulation voltage) may not be efficiently output, depending how to set the reference potential. Thus, in the preferred embodiment, the indifferent electrode pad 39 is characterized in that an area thereof is larger than a total area of the pair of body-surface electrode pads 37, and control processing is executed, for example, based on a first to a fourth voltage application pattern shown in FIG. 6 to FIG. 9.

First, the first pattern shown in FIG. 6 is a case where a minus (−) potential is predominantly given to the first stimulation electrode pad 58. In this case, a reference potential is set to an average potential of the second stimulation electrode pad 59 and the indifferent electrode pad 39. As shown by a dotted line, in a state that the switch portions 54, 56, 61, 62 are turned off and the switch portions 55, 57, 60 are turned on, a voltage is applied so that the second stimulation electrode pad 59 and the indifferent electrode pad 39 will be a positive side (plus side) with respect to the reference potential and so that the first stimulation electrode pad 58 will be a negative side (minus side) with respect to the reference potential. A solid-line arrow in FIG. 6 shows a flow of electric current of the stimulation signal.

Thereby, as shown in FIG. 10A, directly under the second stimulation electrode pad 59 and the indifferent electrode pad 39 (anode), in a subcutaneous tissue 63, within a time during which a voltage is applied, as compared with before application of the voltage, a positive potential is developed. And, negative ions are accumulated inside a cell wall 68 of a nerve cell 67 present directly thereunder, thereby suppressing excitement of the nerve. On the other hand, directly under the first stimulation electrode pad 58 (cathode), in the subcutaneous tissue 63, as compared with before application of the voltage, a negative potential is developed. And, positive ions are accumulated inside the cell wall 68 of the nerve cell 67 present directly thereunder, thereby causing excitement of the nerve. Thus, first capacitors 64, 65 and a second capacitor 66 are provided. First capacitors 64, 65 include the second stimulation electrode pad 59, the indifferent electrode pad 39 (anode) and a skin region in contact with them are given as a counter electrode. The second capacitor 66 includes the first stimulation electrode pad 58 (cathode) and a skin region in contact with it are given as a counter electrode. The first capacitors 64, 65 and the second capacitor 66 are connected in series. Therefore, an applied voltage is distributed to the first capacitors 64, 65 and the second capacitor 66 in inverse proportion to a static capacitance of each of the capacitors 64, 65, 66. Specifically, when the applied voltage is given as V, a static capacitance of the first capacitors 64, 65 and that of the second capacitor 66 are respectively given as a static capacitance C1 (a combined capacity of the first capacitors 64, 65 connected in parallel with each other) and as a static capacitance C2, a voltage of $V \times (C2/(C1+C2))$ is applied to a positive side of each of the first capacitors 64, 65, while a voltage of $V \times (C1/(C1+C2))$ is applied to a negative side of the second capacitor 66. The static capacitances C1 and C2 are increased in proportion to an area of the electrode. Therefore, as described in the preferred embodiment, a total area of the second stimulation electrode pad 59 and the indifferent electrode pad 39 which are given as a reference potential is made larger than an area of the first stimulation electrode pad 58, by which it is possible to make a voltage applied to a negative side of the first stimulation electrode pad 58 relatively larger than a voltage applied to a positive side of each of the second stimulation electrode pad 59 and the indifferent electrode pad 39.

More specifically, where a voltage is applied, with one of the first stimulation electrode pad 58 and the second stimulation electrode pad 59 equal in size to each other being given as a reference potential, the applied voltage is distributed evenly to both of the pads 58, 59, as shown in FIG. 11A. Therefore, it is not true that the voltage of a negative side necessary for an electric stimulation is efficiently output.

In contrast thereto, according to a result of the control processing of the preferred embodiment, as shown in FIG. 11B, it is possible to make a negative side voltage applied to the first stimulation electrode pad 58 relatively larger than a positive side voltage of the second stimulation electrode pad 59 and that of the indifferent electrode pad 39. As a result, a negative side potential which is effective in exciting the nerve is increased, while a positive side potential which is not necessary is decreased. Therefore, it is possible to output a stimulation voltage more efficiently than a conventional device.

In the previously-described invention of Patent Document 1, where the indifferent electrode is not placed in the vicinity of the stimulation electrode but placed in the anterior lower abdomen, etc., as shown in FIG. 10B, a resistance 69 of several kilo ohms is developed as a biological impedance between the stimulation electrode pad 59 and the indifferent electrode pad 39, and a stimulation electric current hardly flows to the indifferent electrode pad 39. As a result, a stimulation voltage is to be applied between the stimulation electrode pads 59 and 58. Unlike the case shown in FIG. 11B, no negative side (minus side) voltage can be predominantly applied to the stimulation electrode pad 59.

Next, the second pattern shown in FIG. 7 is a case that a minus (−) potential is predominantly given to the second stimulation electrode pad 59. In this case, a reference potential is set to an average potential of the first stimulation electrode pad 58 and the indifferent electrode pad 39. As shown by a dotted line, in a state that the switch portions 55, 56, 57, 60 are turned off and the switch portions 54, 61, 62 are turned on a voltage is applied so that the first stimulation electrode pad 58 and the indifferent electrode pad 39 will be a positive side (plus side) with respect to the reference potential and so that the second stimulation electrode pad 59 will be a negative side (minus side) with respect to the reference potential. A solid-line arrow in FIG. 7 shows a flow of electric current of the stimulation signal.

In this control processing as well, a total area of the first stimulation electrode pad 58 and indifferent electrode pad 39 which are given as a reference potential is larger than an area of the second stimulation electrode pad 59. Therefore, a negative side voltage which is applied to the second stimulation electrode pad 59 can be made relatively larger than a positive side voltage which is applied to the first stimulation electrode pad 58 and the indifferent electrode pad 39.

Next, the third pattern shown in FIG. 8 is a case where a minus (−) potential is predominantly given at the same time to the first stimulation electrode pad 58 and the second stimulation electrode pad 59. In this case, a reference potential is set to an average potential of the indifferent electrode pad 39. As shown by a dotted line, in a state that the switch portions 54, 55, 57, 62 are turned off and the switch portions 56, 60, 61 are turned on, a voltage is applied so that the indifferent electrode pad 39 will be a positive side (plus side) with respect to the reference potential and so that the first stimulation electrode pad 58 and the second stimulation electrode pad 59 will be a negative side (minus side) with respect to the reference potential. In FIG. 8, a solid-line arrow shows a flow of electric current of the stimulation signal.

In this control processing as well, an area of the indifferent electrode pad 39 which is given as a reference potential is larger than a total area of the first stimulation electrode pad 58 and the second stimulation electrode pad 59. It is, thus, possible to make a negative side voltage which is applied to the first stimulation electrode pad 58 and the second stimulation electrode pad 59 relatively larger than a positive side voltage which is applied to the indifferent electrode pad 39.

Next, the fourth pattern shown in FIG. 9 is a case where a minus (−) potential is predominantly given to the first stimulation electrode pad 58 (indifferent electrode reference). In this case, a reference potential is set to an average potential of the indifferent electrode pad 39. As shown by a dotted line, in a state that the switch portions 54, 55, 57, 61, 62 are turned off and the switch portions 56, 60 are turned on, a voltage is applied so that the indifferent electrode pad 39 will be a positive side (plus side) with respect to the reference potential and so that the first stimulation electrode pad 58 will be a negative side (minus side) with respect to the reference potential. A solid-line arrow in FIG. 9 shows a flow of electric current of the stimulation signal.

In this control processing as well, an area of the indifferent electrode pad 39 which is given as a reference potential is larger than an area of the first stimulation electrode pad 58. Therefore, it is possible to make a negative side voltage which is applied to the first stimulation electrode pad 58 relatively larger than a positive side voltage which is applied to the indifferent electrode pad 39.

Second Preferred Embodiment

Figure 12A:
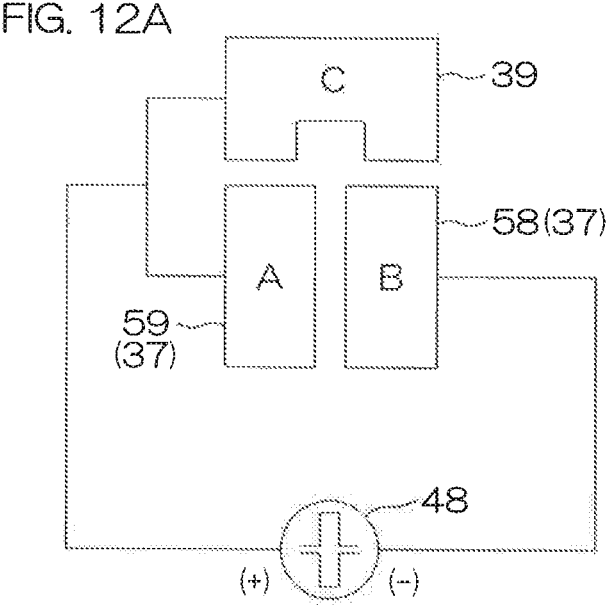
FIG. 12A is a drawing which shows one example of an electric configuration when a voltage is applied to each of the electrodes of the urination disorder treatment device.
Figure 12B:
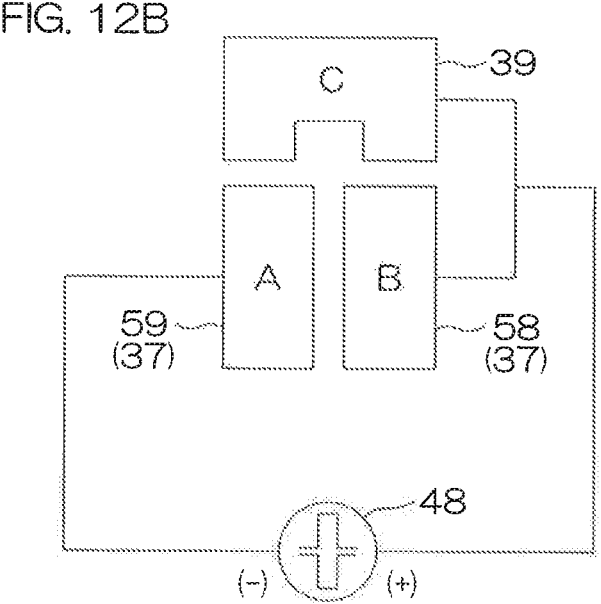
FIG. 12B is a drawing which shows one example of an electric configuration when a voltage is applied to each of the electrodes of the urination disorder treatment device.

As described above, the urination disorder treatment device 31 is controlled, for example, by an alternating pulse pattern in which a voltage pulse that the first stimulation electrode pad 58 will be a negative side with reference to FIG. 12A (a voltage pulse in which the second stimulation electrode pad 59 and the indifferent electrode pad 39 will be a positive side) and a voltage pulse that the second stimulation electrode pad 59 will be a negative side with reference to FIG. 12B (in which the first stimulation electrode pad 58 and the indifferent electrode pad 39 will be a positive side) are alternately generated. That is, in this example, the control shown in FIG. 6 and that shown in FIG. 7 are executed alternately and, the pulse patterns found in the above instances are shown in FIG. 13A to FIG. 13C.

FIG. 13A is a drawing which shows a pulse pattern of the first stimulation electrode pad 58, FIG. 13B is a drawing which shows a pulse pattern of the second stimulation electrode pad 59, and FIG. 13C is a drawing which shows a pulse pattern of the indifferent electrode pad 39. In FIG. 13A to FIG. 13C, "A," "B" and "C" show the respective areas of the first stimulation electrode pad 58, the second stimulation electrode pad 59 and the indifferent electrode pad 39. "V" shows an applied voltage.

With reference to FIG. 13A to FIG. 13C, in the control of these pulse patterns, a positive side voltage is constantly applied to the indifferent electrode pad 39. Therefore, the indifferent electrode pad 39 is easily subjected to deterioration due to electrolysis, and the indifferent electrode pad 39 may be shorter in life than the first stimulation electrode pad 58 or the second stimulation electrode pad 59.

Thus, in the preferred embodiment shown in FIG. 13D and FIG. 13E, during a period of time of T between a pulse 74 and a pulse 75 with regard to the indifferent electrode pad 39 and a pulse 74 and a pulse 75 occurring in a next cycle, a voltage is applied to the first stimulation electrode pad 58, the second stimulation electrode pad 59 and the indifferent electrode pad 39 so as to generate a corrected pulse 76, a corrected pulse 77, a corrected pulse 78 and a corrected pulse 79. The corrected pulse 76 is obtained by inverting a polarity of a pulse 71 with regard to a reference potential and the corrected pulse 78 is obtained by inverting a polarity of a pulse 70 with regard to the reference potential. The corrected pulse 77 is obtained by inverting a polarity of a pulse 73 with regard to the reference potential and a corrected pulse 79 is obtained by inverting a polarity of a pulse 72 with regard to the reference potential. Thereby, it is possible to cancel any influence on the indifferent electrode pad 39 due to a continuous application of the voltage to the positive side. Further, it is possible to completely cancel any influence due to a greater output of the stimulation to the negative side of the first stimulation electrode pad 58 and that of the second stimulation electrode pad 59, and it is also possible to suppress deterioration of all the electrode pads.

For example, complete cancellation of a voltage applied to both the positive and negative sides of each of the first stimulation electrode pad 58, the second stimulation electrode pad 59 and the indifferent electrode pad 39 can be attained by a procedure that a magnitude of voltage of the pulse 74 is subjected to time integration, and a magnitude of voltage V1 of the corrected pulses 76 to 79, and an application time, T1, T2, may be determined so as to give an integration value equal to the thus obtained value. For example, where an interval time at which the stimulation is repeated is given as T, a time at which a corrected pulse can be output is a time T1 and a time T2 excluding a time ΔT for switching a positive and a negative output of the stimulation. Next, voltages of the corrected pulses 76 to 79 are such that V×t1 which is obtained by multiplying an applied voltage V to be corrected by an application time t1 is given as V1 that is an opposite polarity of the voltage divided by the application time T1 and T2 of the corrected pulse, thereby expressing—(V×t1)/T1 and −(V×t2)/T2, and may be output to the corrected pulses 76 to 79.

The application time T1 or T2 of the corrected pulse is a longer time than t1 or t2, and the applied voltage V1 can be made smaller than an applied voltage V of treatment stimulation, thereby preventing an influence on the treatment menu suitable for a person to be treated. Further, this can be realized only by applying V1 in place of the applied voltage V and giving the application time as T1 or T2, without any addition of a special circuit to an output circuit when the applied voltage V is output.

Although no illustration is given in FIG. 13D or FIG. 13E, the voltage applied to the indifferent electrode pad 39 is the same voltage as that applied to the plus side in FIG. 13D or FIG. 13E. In other words, this is because a plus side voltage in FIG. 13D or FIG. 13E is applied to an electrode with a combination of A+C and B+C (C is the indifferent electrode pad 39). Therefore, if a voltage in which a plus side voltage in FIG. 13D or FIG. 13E is inverted in polarity, that is, a minus voltage, is applied to the combination of A+C and B+C, the indifferent electrode pad 39 is to be cancelled.

Third Preferred Embodiment

A method for suppressing deterioration of the indifferent electrode pad 39 may include control processing shown next in the third preferred embodiment below, in addition to the control processing shown in the second preferred embodiment described above. More specifically, with reference to FIG. 14A to FIG. 14C, after the stimulation control processing according to a pulse pattern shown by pulses 70 to 75 has been repeated several times, there is provided a period of time during which a voltage is applied to the first stimulation electrode pad 58, the second stimulation electrode pad 59 and the indifferent electrode pad 39. In the period, a pulse pattern which is opposite to the pulse pattern shown by the pulses 70 to 78 in terms of positive and negative voltages is developed. That is, a corrected pulse 80 and a corrected pulse 81 which are opposite to the pulse 70 and the pulse 71 in terms of positive and negative voltages are applied to the first stimulation electrode pad 58. A corrected pulse 82 and a corrected pulse 83 which are opposite to the pulse 72 and the pulse 73 in terms of positive and negative voltages are applied to the second stimulation electrode pad 59. A corrected pulse 84 and a corrected pulse 85 which are opposite to the pulse 74 and the pulse 72 in terms of positive and negative voltage are applied to the indifferent electrode pad 39.

Thereby, any influence on the indifferent electrode pad 39 due to a continuous application of a positive-side voltage can be partially canceled to suppress deterioration of the indifferent electrode pad 39. In this control processing as well, upon application of the corrected pulse 84 and the corrected pulse 85, it is not necessary to electrically detach the indifferent electrode pad 39 from the first stimulation electrode pad 58 or the second stimulation electrode pad 59, thus making it possible to prevent an electric circuit from being complicated.

A description has been so far given of the preferred embodiments of the present invention. However, the present invention can be carried out in other modes.

Fourth Preferred Embodiment

For example, in the first preferred embodiment described above, a description has been given of a configuration of the portable-type urination disorder treatment device 31. An electric configuration of the urination disorder treatment device and control thereof may be applied to a stationary type urination disorder treatment device 31 in which a monitor is separated from a main body of the treatment device.

Fifth Preferred Embodiment

Further, in the first preferred embodiment described above, as an example of the display portion of the present invention, there is shown the monitor 33 which displays a message or an image for a user. However, a means for displaying an operating state of the urination disorder treatment device 31 for a user is not necessarily limited to the monitor 33. For example, a message to a person to be treated (for example, an error message or an incorrect position at which the electrode is attached) may be in advance printed on a front panel of the body 32 to illuminate characters thereof by using an LED, etc., or to switch on a lamp near the characters, so that the person to be treated can be informed.

Sixth Preferred Embodiment

Further, in the first preferred embodiment described above, only the urination disorder treatment device 31 is adopted as an example of the electrical stimulation treatment device. However, the present invention is not limited to the urination disorder treatment device but can be applied to devices in general which are used in electrical stimulation therapy for diseases other than a urination disorder.

Seventh Preferred Embodiment

Further, in the first preferred embodiment described above, the circuit portion 49 is configured with semiconductor integrated circuit chips but may be configured with individual components, for example, a semiconductor switch (MOSFET, etc.,) which is turned on by application of a gate voltage and a semiconductor relay.

Eighth Preferred Embodiment

Further, in the first preferred embodiment described above, a connection is made by using the pair of body-surface electrode pads 37 and the indifferent electrode pad 39 which are female terminals and using the insulation cable 36 and the insulation cable 38 which are male terminals. The terminals used for this connection may be a pair of male and female terminals. Therefore, the terminal of the pair of body-surface electrode pads 37 or that of the indifferent electrode pad 39 may not be necessarily a female terminal but may be a male terminal. In this case, the terminal of the insulation cable 36 or that of the insulation cable 38 may only be a female terminal.

Ninth Preferred Embodiment

Further, in the first preferred embodiment described above, a connection between the pair of body-surface electrode pads 37 and the indifferent electrode pad 39 and a connection between the insulation cables 36, 38 are made by using the magnet terminals (magnetic connection portions). However, these portions are only required to be electrically connected and, for example, may also be electrically connected by male/female terminals (electric connection portions) which are not magnets. They are not necessarily connected so as to be attached or detached freely. For example, a connection between the pair of body-surface electrode pads 37 and the insulation cable 36 and a connection between the indifferent electrode pad 39 and the insulation cable 38 may be each made integrally.

Tenth Preferred Embodiment

Figure 15A:
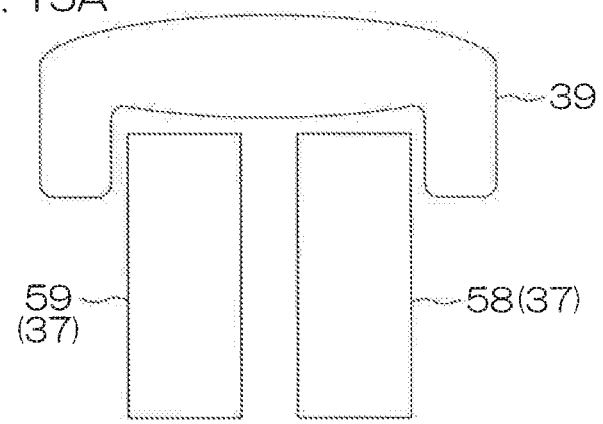
FIG. 15A is a drawing which describes a variation of the shape of an electrode pad.
Figure 15B:
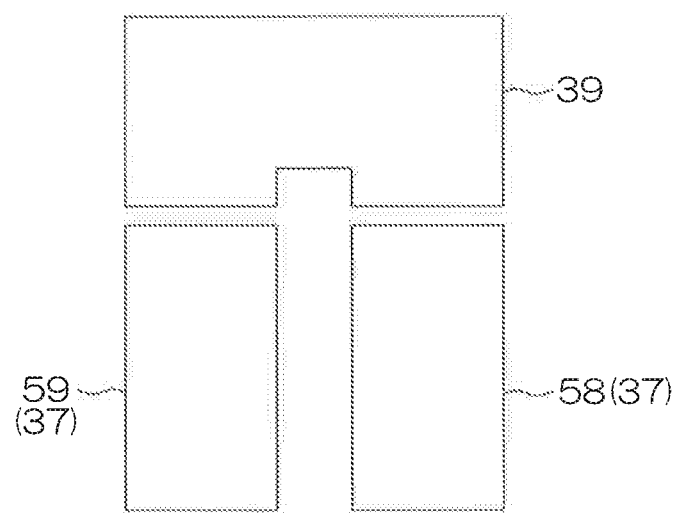
FIG. 15B is a drawing which describes a variation of the shape of the electrode pad.

For example, in the first preferred embodiment described above, as shown in FIG. 15A, the indifferent electrode pad 39 is formed so that it is mostly defined by a curve and disposed so as to surround partially the first stimulation electrode pad 58 and the second stimulation electrode pad 59 (an upper part in FIG. 15A). However, as shown in FIG. 15B, it may be formed so that it is defined by a straight line and may be disposed so as not to overlap with the first stimulation electrode pad 58 or the second stimulation electrode pad 59.

Eleventh Preferred Embodiment

Further, with reference to FIG. 16, the body-surface electrode pad 37 and the indifferent electrode pad 39 may be arranged by a combination of an electrode portion 23 and a pad portion 24.

The electrode portion 23 includes a pair of stimulation electrodes 25 and an indifferent electrode 26 in an integral manner. In the preferred embodiment, the pair of stimulation electrodes 25 and the indifferent electrode 26 are each formed to have a raised portion 27 or 28 on a surface thereof and disposed in a triangular manner so as to integrate the electrodes which are mutually adjacent. Each of the electrodes 25, 26 may be arranged so that a metal plate having the raised portion 27 or 28 will be covered with rubber or the like.

The pad portion 24 includes a base portion 29 and a gel 30 placed on the base portion. The gel 30 is provided one each for the pair of stimulation electrodes 25 and the indifferent electrode 26 and, therefore, disposed in a triangular manner.

In using the body-surface electrode pad 37 and the indifferent electrode pad 39, for example, first, each of the gels 30 is adhered on the electrode portion 23 so that each of the stimulation electrode 25 and the indifferent electrode 26 overlaps with each of the gels 30. Then, the base portion 29 may be detached from the electrode portion 23 to which each of the gels 30 is adhered and then adhered on the skin of a person to be treated. Further, after the use, the base portion 29 is again adhered to the electrode portion 23 to which each of the gels 30 has been adhered, thus making it possible to protect each of the gels 30 until it is used again.

Twelfth Preferred Embodiment

Figure 17:
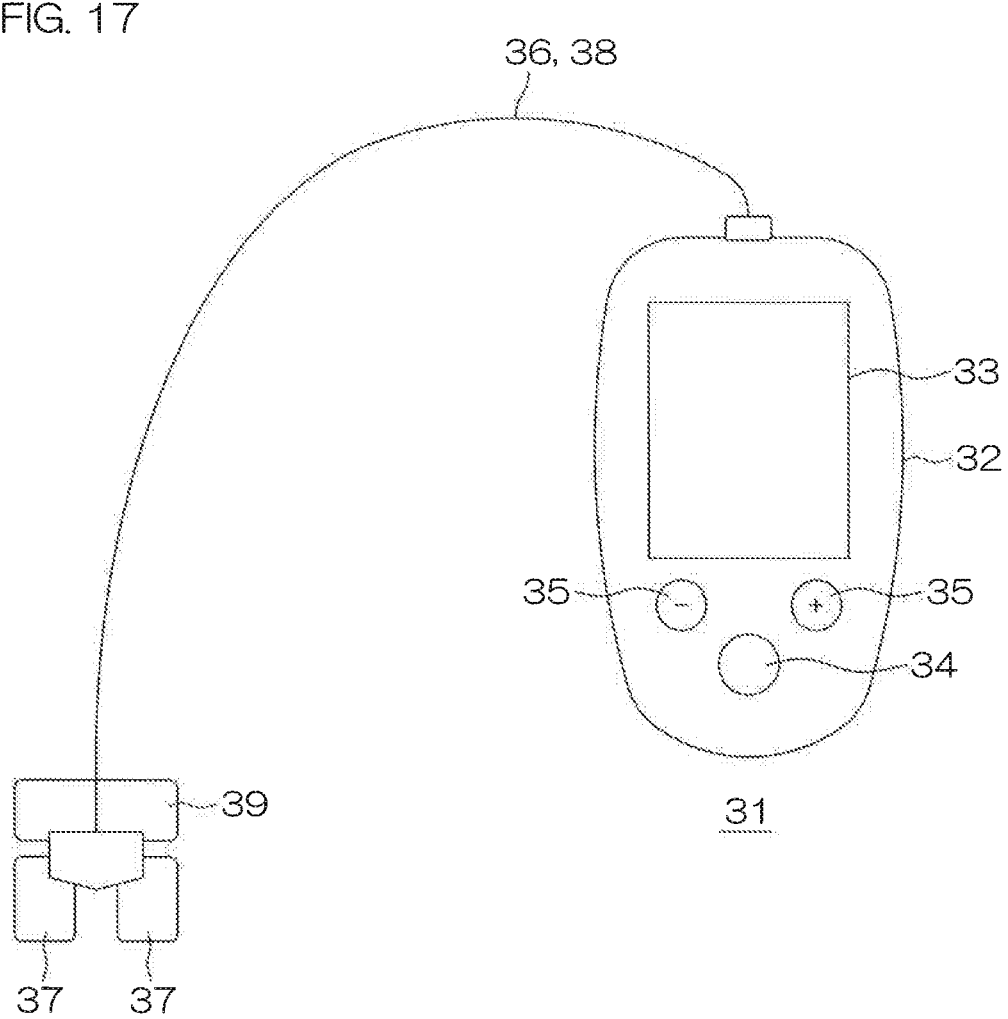
FIG. 17 is a drawing which describes a variation of the mode of the urination disorder treatment device.

Further, with reference to FIG. 17, the urination disorder treatment device 31 may be provided with a substantially oval-shaped body 32. The monitor 33 may be formed in a rectangular shape longer along a longitudinal direction of the body 32 and disposed so as to be closer to one end of the body 32 in the longitudinal direction. The start/stop button 34 and the plurality of operation buttons 35, 35 may be disposed on the other end side of the body 32 in the longitudinal direction with respect to the monitor 33.

Thirteenth Preferred Embodiment

Figure 18:
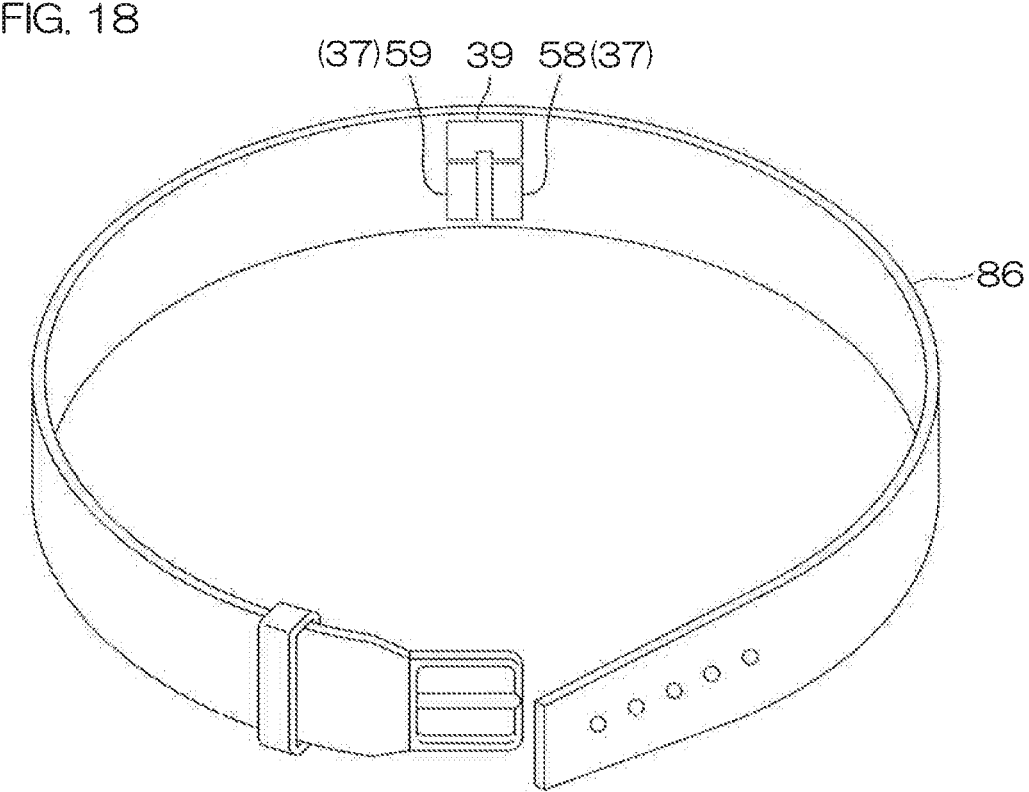
FIG. 18 is a schematic view of the urination disorder treatment device according to a preferred embodiment of the present invention.

Further, with reference to FIG. 18, as a means for attaching the pair of body-surface electrode pads 37 (first stimulation electrode pad 58 and the second stimulation electrode pad 59) and the indifferent electrode pad 39, there may be adopted a belt tied around the waist. The pair of body-surface electrode pads 37 and the indifferent electrode pad 39 may be disposed, for example, at the back (a side with which the body is in contact) of a belt 86.

In addition, the design of the present invention may be modified in various ways without departing from the scope described in the claims.

The present application corresponds to Japanese Patent Application No. 2017-181345 filed in the Japan Patent Office on Sep. 21, 2017 and Japanese Patent Application No. 2018-089397 filed on May 7, 2018, and the entire disclosure of this application is incorporated herein by reference.

REFERENCE SIGNS LIST

1: Human body
2: Vertebral column
3: Sacral bone
4: Lumbar vertebra
5: First sacral foramen
6: Second sacral foramen
7: Third sacral foramen 8: Fourth sacral foramen
9: Bladder
10: Internal urethral sphincter
11: External urethral sphincter
12: Hypogastric nerve
13: Pelvic nerve
14: Pudic nerve
15: Ischiadic nerve
16: Peroneal nerve
17: Tibial nerve
18: First toe (big toe)
19: Second toe
20: Third toe
21: Fourth toe
22: Fifth toe (little toe)
23: Electrode portion
24: Pad portion
25: Stimulation electrode
26: Indifferent electrode
27: Raised portion
28: Raised portion
29: Base portion
30: Gel
31: Urination disorder treatment device
32: Body
33: Monitor
34: Start/stop button
35: Operation button
36: Insulation cable
37: Body-surface electrode pad
38: Insulation cable
39: Indifferent electrode pad
40: Magnet adaptor
41: Magnet adaptor
42: Male terminal
43: Male terminal
44: Magnet port
45: Magnet port
46: Female terminal
47: Female terminal
48: Control portion
49: Circuit portion
50: Plus side terminal
51: Plus side wiring
52: Minus side terminal
53: Minus side wiring
54: Switch portion
55: Switch portion
56: Switch portion
57: Switch portion
58: First stimulation electrode pad
59: Second stimulation electrode pad
60: Switch portion
61: Switch portion
62: Switch portion
63: Subcutaneous tissue
64: First capacitor
65: First capacitor
66: Second capacitor
67: Nerve cell
68: Cell wall
69: Resistance
70: Pulse
71: Pulse
72: Pulse
73: Pulse
74: Pulse
75: Pulse
76: Corrected pulse
77: Corrected pulse
78: Corrected pulse
79: Corrected pulse
80: Corrected pulse
81: Corrected pulse
82: Corrected pulse
83: Corrected pulse
84: Corrected pulse
85: Corrected pulse
86: Belt

The invention claimed is:

1. An electric stimulation treatment device comprising:
a pair of application electrodes configured to be disposed at a site of the skin of a person to be treated where an electric stimulation is to be given and which supply an electric stimulation signal to the skin;
an indifferent electrode configured to be disposed in a vicinity of a site where the electric stimulation is to be given on the same skin surface as the site where the electric stimulation is to be given; and
a control portion which supplies an electric signal to the pair of application electrodes and the indifferent electrode, wherein
the control portion executes,
the stimulation signal as an output from one of the pair of application electrodes with respect to a reference potential set to an average potential of the other of the pair of application electrodes and the indifferent electrode.

2. The electric stimulation treatment device according to claim 1, wherein
the pair of application electrodes are mutually equal in area, and
the indifferent electrode has an area which is 0.25 to 10 times larger than each of the application electrodes.

3. The electric stimulation treatment device according to claim 1, wherein
the control portion executes the stimulation signal output by supplying an electric signal which generates a predetermined pulse pattern, and
the control portion also supplies, between adjacent pulses, to the indifferent electrode an electric signal which generates a negative-side voltage pulse with respect to the reference potential.

4. The electric stimulation treatment device according to claim 1, wherein
the pair of application electrodes include a first stimulation electrode and a second stimulation electrode,
the control portion controls the output in an alternating pulse pattern which alternately generates a first pattern and a second pattern, in the first pattern, a voltage pulse being generated so that the first stimulation electrode will be a negative side and the second stimulation electrode and the indifferent electrode will be a positive side with respect to a reference potential set to an average potential of the second stimulation electrode and the indifferent electrode, and in the second pattern, a voltage pulse being generated so that the second stimulation electrode will be a negative side and the first stimulation electrode and the indifferent electrode will be a positive side with respect to a reference potential set to an average potential of the first stimulation electrode and the indifferent electrode, and
the control portion also applies a voltage to the first stimulation electrode, the second stimulation electrode and the indifferent electrode so as to generate, between the second pattern and the first pattern which is a next cycle, a corrected pulse in which a pulse of each of the first stimulation electrode, the second stimulation electrode and the indifferent electrode in the first pattern and a pulse of each of the first stimulation electrode, the second stimulation electrode and the indifferent electrode in the second pattern are inverted in terms of a polarity of each of them.

5. The electric stimulation treatment device according to claim 1, wherein
the control portion executes the stimulation signal output by supplying an electric signal which generates a predetermined pulse pattern, and
the control portion also supplies, after the stimulation signal processing, to the pair of application electrodes and the indifferent electrode an electric signal so as to generate a pulse pattern which is inverted in positive voltage and negative voltage to the pulse pattern.

6. The electric stimulation treatment device according to claim 1, wherein,
the pair of application electrodes include a pair of application electrodes which are disposed side by side at the back of a sacrum of a person to be treated to supply an electric stimulation signal from the back of the sacrum, and
the indifferent electrode includes an indifferent electrode configured to be disposed in a vicinity of a pair of application electrodes at the back of the sacrum.

7. The electric stimulation treatment device according to claim 1 further comprising:
a main body of a treatment device;
a wiring portion which connects the mainbody of the treatment device with the pair of application electrodes; and
a magnetic connection portion which magnetically connects the wiring portion with the pair of application electrodes.

8. An electric stimulation treatment device comprising:
a pair of application electrodes configured to be disposed at a site of the skin of a person to be treated where an electric stimulation is to be given and which supply an electric stimulation signal to the skin;
an indifferent electrode configured to be disposed in a vicinity of a site where the electric stimulation is to be given; and
a control portion which supplies an electric signal to the pair of application electrodes and the indifferent electrode, wherein
the control portion executes the stimulation signal as an output from any one of the following components, that is,
(1) one of the pair of application electrodes with respect to a reference potential set to an average potential of the other of the pair of application electrodes and the indifferent electrode,
(2) both of the pair of application electrodes with respect to a reference potential set to the indifferent electrode, or
(3) one of the pair of application electrodes with respect to a reference potential set to the indifferent electrode,
wherein the control portion executes the stimulation signal output by supplying an electric signal which generates a predetermined pulse pattern, and
the control portion also generates a negative-side voltage pulse with respect to the reference potential by supplying, between adjacent pulses, to the indifferent electrode an electric signal.

9. The electric stimulation treatment device according to claim 8, wherein
the pair of application electrodes are mutually equal in area, and
the indifferent electrode has an area which is 0.25 to 10 times larger than each of the application electrodes.

10. The electric stimulation treatment device according to claim 8 which includes an operation portion by which a user selects any one of the components to be used among the stimulation signal output of (1), (2) and (3) of the control portion.

11. An electric stimulation treatment device comprising:
a pair of application electrodes configured to be disposed at a site of the skin of a person to be treated where an electric stimulation is to be given and which supply an electric stimulation signal to the skin;
an indifferent electrode configured to be disposed in a vicinity of a site where the electric stimulation is to be given; and
a control portion which supplies an electric signal to the pair of application electrodes and the indifferent electrode, wherein
the control portion executes the stimulation signal as an output from any one of the following components, that is,
(1) one of the pair of application electrodes with respect to a reference potential set to an average potential of the other of the pair of application electrodes and the indifferent electrode,
(2) both of the pair of application electrodes with respect to a reference potential set to the indifferent electrode, or
(3) one of the pair of application electrodes with respect to a reference potential set to the indifferent electrode, wherein
the pair of application electrodes include a first stimulation electrode and a second stimulation electrode,
the control portion
alternatively generates a first pattern and a second pattern by controlling the output in an alternating pulse pattern,
in the first pattern, generating a voltage pulse so that the first stimulation electrode will be a negative side and the second stimulation electrode and the indifferent electrode will be a positive side with respect to a reference potential set to an average potential of the second stimulation electrode and the indifferent electrode, and
in the second pattern, generating a voltage pulse so that the second stimulation electrode will be a negative side and the first stimulation electrode and the indifferent electrode will be a positive side with respect to a reference potential set to an average potential of the first stimulation electrode and the indifferent electrode, and
the control portion also applies a voltage to the first stimulation electrode, the second stimulation electrode and the indifferent electrode so as to generate, between the second pattern and the first pattern which is a next cycle, a corrected pulse in which a pulse of each of the first stimulation electrode, the second stimulation electrode and the indifferent electrode in the first pattern and a pulse of each of the first stimulation electrode, the second stimulation electrode and the indifferent electrode in the second pattern are inverted in terms of a polarity of each of them.

12. An electric stimulation treatment device comprising:
a pair of application electrodes configured to be disposed at a site of the skin of a person to be treated where an electric stimulation is to be given and which supply an electric stimulation signal to the skin;
an indifferent electrode configured to be disposed in a vicinity of a site where the electric stimulation is to be given; and
a control portion which supplies an electric signal to the pair of application electrodes and the indifferent electrode, wherein
the control portion executes the stimulation signal as an output from any one of the following components, that is,
(1) one of the pair of application electrodes with respect to a reference potential set to an average potential of the other of the pair of application electrodes and the indifferent electrode,
(2) both of the pair of application electrodes with respect to a reference potential set to the indifferent electrode, or
(3) one of the pair of application electrodes with respect to a reference potential set to the indifferent electrode, wherein
the control portion executes the stimulation signal output by supplying an electric signal which generates a predetermined pulse pattern, and
the control portion also generates a pulse pattern which is inverted in positive voltage and negative voltage to the pulse pattern by supplying, after the stimulation signal processing, to the pair of application electrodes and the indifferent electrode an electric signal.

* * * * *